United States Patent
Borzatta et al.

(10) Patent No.: US 8,809,389 B2
(45) Date of Patent: Aug. 19, 2014

(54) SUBSTITUTED ALKYNYL PHENOXY COMPOUNDS AS NEW SYNERGISTS IN PESTICIDAL COMPOSITIONS

(75) Inventors: Valerio Borzatta, Bologna (IT); Elisa Capparella, Ravenna (IT); Leni Moroni, Noceto (IT); Graham Moores, Stevenage (GB); Despina Philippou, Nicosia (CY)

(73) Assignees: Endura S.p.A. (IT); Rothamsted Research Ltd. (GB)

( * ) Notice: Subject to any disclaimer, the term of this patent is extended or adjusted under 35 U.S.C. 154(b) by 0 days.

(21) Appl. No.: 13/391,496

(22) PCT Filed: Aug. 18, 2010

(86) PCT No.: PCT/EP2010/062019
§ 371 (c)(1),
(2), (4) Date: Feb. 21, 2012

(87) PCT Pub. No.: WO2011/020848
PCT Pub. Date: Feb. 24, 2011

(65) Prior Publication Data
US 2012/0208874 A1    Aug. 16, 2012

(30) Foreign Application Priority Data
Aug. 18, 2009   (EP) .................................... 09168083

(51) Int. Cl.
| | | |
|---|---|---|
| *A01N 43/30* | (2006.01) | |
| *A01N 31/14* | (2006.01) | |
| *C07C 43/215* | (2006.01) | |
| *C07C 41/16* | (2006.01) | |

(52) U.S. Cl.
CPC .............. *C07C 41/16* (2013.01); *C07C 43/215* (2013.01); *A01N 43/30* (2013.01)
USPC ............ 514/464; 514/469; 549/464; 549/470

(58) Field of Classification Search
CPC ....... A01N 43/30; A01N 51/00; A01N 53/00; C07C 41/16; C07C 43/215
USPC ................... 514/464, 469, 720; 549/464, 470
See application file for complete search history.

(56) References Cited

U.S. PATENT DOCUMENTS

| | | | |
|---|---|---|---|
| 3,423,428 A * | 1/1969 | Rachlin Albert Israel et al. | 549/437 |
| 3,524,915 A * | 8/1970 | Rachlin Albert Israel et al. | 514/465 |
| 2005/0191238 A1 | 9/2005 | Casebier et al. | |

OTHER PUBLICATIONS

Contribution from the Entomology Research Division, Agricultural Research Service, U.S. Department of Agriculture; Synthesis of Methylenedioxyphenyl Compounds from Isosafrole and Sesamol, B.H. Alexander, S.I. Gertler, R.T. Brown, T.A. Oda, and M. Beroza Oct. 1959 pp. 1504-1507.
Chemistry—A European Journal; Intramolecular Hydroarylation of Alkynes Catalyzed by Platinum or Gold: Mechanism and endo Selectivity, Cristina Nevada and Antonio M. Echavarren, Chem. Eur. J. 2005, 11, pp. 3155-3164.
The Florida Entomologist vol. 47, No. 3, 1974; Chemosterilant Activity of 75 Compounds Against the Tobacco Budworm; D.A. Wolfenbarger, Eliud Cantu, A.A. Guerra, J. G. Pomonis, S.H. Robinson, and R.D. Garcia; Cotton Insects Research Laboratory, Agrc. Res. Serv., USDA, Brownsville, Texas; pp. 287-295.
G. Brooks, A. Ottridge, R. Jennings, D. Mace & B. Alexander; "The Effect of 2,2-Dimethylchromene derivatives and some other compounds on the development of Oncopeltus fasciatus (Dallas) and Locusta migratoria migratorioides (R&F)," Pesticide Science, vol. 16, No. 6, 1985, pp. 571-588, XP002557135.

* cited by examiner

*Primary Examiner* — Janet Epps-Smith
*Assistant Examiner* — Courtney Brown
(74) *Attorney, Agent, or Firm* — Gifford, Krass, Sprinkle, Anderson & Citkowski, P.C.

(57) ABSTRACT

A composition comprising an alkynyl phenoxy compound of Formula (I) as a synergist and a pesticidal active ingredient is described, wherein $R_1$ and $R_2$, similar or different, are ($C_1$-$C_4$)alkyl or $R_1O$— and $R_2O$— together represent a group —O—$CH_2$—O—, —O—$CH(CH_3)$—O, —O—$CH_2$—$CH_2$—O—, —O—$CH_2$—$CH_2$—, $R_3$ is ($C_1$-$C_6$)alkyl, ($C_3$-$C_6$)alkenyl or —B—($CH_2$—$CH_2$—O)z-$R_6$ where B is —$CH_2$—O— or —O—, z is 0, 1 or 2 and $R_6$ is ($C_1$-$C_4$)alkyl; $R_4$ is hydrogen or methyl; $R_5$ is hydrogen or methyl; x is an integer from 1 to 2; y is 0, 1 or 2; with the proviso that when $R_3$ is —B—($CH_2CH_2$—O)z-$R_6$, y is 1 and 5-(propargyloxy)-benzo[1,3]dioxole is excluded.

22 Claims, 3 Drawing Sheets

SUBSTITUTED ALKYNYL PHENOXY COMPOUNDS AS NEW SYNERGISTS IN PESTICIDAL COMPOSITIONS

CROSS-REFERENCE TO RELATED APPLICATIONS

This application is the U.S. National Phase of PCT/EP2010/062019 filed Aug. 18, 2010, which claims priority of European Patent Application 09168083.5 filed Aug. 18, 2009.

FIELD OF THE INVENTION

The present invention relates to a pesticidal composition comprising substituted alkynyl phenoxy compounds as synergist and a pesticidal active ingredient in all stereochemical configurations.

BACKGROUND OF THE INVENTION

Compounds which are no toxic or only slightly toxic against pests, but in combination with active ingredients can give a new product active against pests, having an effectiveness significantly greater than the sum of the components when used separately, are named synergists.

These compounds may in principle act in several ways, but one of the main mechanisms reported in the art is the interaction with the metabolism of the active substance. Metabolism can proceed through oxidative, hydrolytic, conjugative and absorption reactions and possible variations thereof.

On the basis of the discovery of synergists and of their way of actions, a wide range research and development started from the mid 60', thus giving products that were interesting for scientific research, but only a few for market purposes. One of the most effective and widely used synergists is represented by piperonyl butoxide (5-4[[2-(2-butoxyethoxy)]methyl]-6-propyl-1,3-benzodioxole), claimed in U.S. Pat. No. 2,550,737.

Piperonyl butoxide is claimed to give a synergistic effect in combination with pyrethrins as well as pyrethroids such as allethrin, prallethrin, tetramethrin and so on. Other synergists have been proposed such as MGK 264 (N-2-ethylhexylbicyclo[2.2.1]-5-heptene-2,3-dicarboximide) reported by Moore J. B. in Proceed. Mid-Year Meeting, Chem. Spec. Manuf. Ass.(1950), June, 72. Among different synergists, alkynyl derivatives were cited to give synergistic effect when in composition with pyrethroids or other active ingredients against pests. These alkynyl compounds generally belong to two different families, being the first one represented by phenyl alkynyl ethers and the second one by benzyl alkynyl ethers. Other families can be represented, by instance, by N-(omega-alkynyl)phtalimides as claimed in GB 1,038,693; naphtalenecarboxylic acid esters of alkynyl alcohol as claimed in U.S. Pat. No. 4,291,058 as insecticides and acaricides; oxime alkynyl ethers as claimed in U.S. Pat. No. 3,980,799 as synergists in combination with phosphoric esters, carbamates and pyrethroids. Among the first chemical family (phenyl alkynyl ethers) we can mention phenyl-2-propynyl ethers with a synergistic effects against pests when used in combination with carbamates (Fellig J. in J. Agr. Food. Chem.,18(1), 78-80); U.S. Pat. Nos. 3,423,428 and 3,524,915 which claim methylenedioxy propynyl ethers with a synergistic effect in combination with carbamates; U.S. Pat. No. 3,777,024 which claims aryl propargyl ethers and thioethers as synergists in combination with phosphoric esters, nitrophenols and chlorinated hydrocarbon.

Among the second family (benzyl propynyl ethers) U.S. Pat. No. 3,880,999 can be mentioned, which claims benzyl 2-propynyl ethers to enhance the activity of pyrethroids and phosphoric esters; U.S. Pat. No. 6,277,867, WO1998/22416 and WO1998/22417 which claim benzyl alkynyl ethers as synergists in combination with pyrethroids and carbamates and the process thereof.

Nevertheless all these products didn't satisfy completely the synergistic activities and new synergistic compounds were needed.

The object of the present invention is therefore to provide synergistic compounds having a high activity against pests in combination with different active ingredients.

BRIEF SUMMARY OF THE INVENTION

This object has been achieved by providing a pesticidal composition comprising an alkynyl phenoxy compound containing at least one alkynyl group, able to increase the effect of the pesticides through a biochemical actions on pest enzymatic systems. Therefore the present invention relates to a pesticidal composition comprising an alkynyl phenoxy compound of formula (I):

wherein
$R_1$ and $R_2$, similar or different, are $(C_1$-$C_4)$alkyl or $R_1O$— and $R_2O$— together represent a group —O—$CH_2$—O—, —O—CH($CH_3$)—O—, —O—$CH_2$—$CH_2$—O—, —O—$CH_2$—$CH_2$—,
R3 is $(C_1$-$C_6)$alkyl, $(C_3$-$C_6)$alkenyl or —B—($CH_2$—$CH_2$—O)z-$R_6$ where B is —$CH_2$—O— or —O—,
z is 0, 1 or 2 and $R_6$ is $(C_1$-$C_4)$alkyl;
$R_4$ is hydrogen or methyl;
$R_5$ is hydrogen or methyl;
x is an integer from 1 to 2
y is 0, 1 or 2
with the proviso that
when R3 is —B—($CH_2$—$CH_2$—O)z—$R_6$, y is 1 and 5-(propargyloxy)-benzo[1,3]dioxole is excluded,
as a synergist and a pesticidal active ingredient.

In the present invention when the term "synergist" is used it is intended a compound capable to increase the activity of a pesticidal active ingredient.

In the present invention an alkynyl phenoxy compound of formula (I) comprises in its definition also all its stereochemical configurations.

In the formula (I) the term alkyl is used it means linear or branched alkyl.

For instance a pesticidal active ingredient can belong to different classes such as pyrethroids, neonicotinoids, carbamates, phosphoric esters and so on.

In a further aspect the invention relates to a new compound selected from the group consisting of 5-(but-2-ynyloxy)-benzo[1.3]dioxole, 5-(but-2-ynyloxy)-6-propyl-benzo[1.3]dioxole, 1-(propargyloxy)-6-propyl-3,4-dimethoxybenzene, 1-(but-2-ynyloxy)-6-propyl-3,4-dimethoxybenzene, 5-[2-(2- butoxyethoxy)-ethoxy]methyl-6-(but-2-ynyloxy)-benzo[1.3]dioxole, 5-(but-2-ynyloxy)-2,3-dihydrobenzofuran, 6-(but-2-ynyloxy)-5-propyl-2,3-dihydrobenzofuran.

The invention also relates to pesticide formulation comprising the pesticide composition of the present invention and an inert carrier.

Furthermore the present invention relates to a method for controlling pests by applying an effective amount of the present compounds and pesticidal active ingredients, i.e. the pesticidal composition, to the pests both by applying earlier the present compounds and later on the active ingredients and by the contemporaneous administration of the present compounds and active ingredients as encapsulated formulations, being these one able to release the present compounds immediately and the active ingredients after some time.

In another aspect the invention therefore relates to a method for controlling pests which provides for applying an efficacy amount of the composition according to the present invention to pests on non animal biotopes.

In a further aspect the invention relates to a use of the composition according to the present invention for the manufacture of a pesticide in the treatment of pests on animal biotopes.

DETAILED DESCRIPTION OF THE INVENTION

The present invention relates to a pesticidal composition comprising an alkynyl phenoxy compound of formula (I):

wherein
$R_1$ and $R_2$, similar or different, are $(C_1-C_4)$alkyl or $R_1O$— and $R_2O$— together represent a group —O—CH$_2$—O—, —O—CH(CH$_3$)—O—, —O—CH$_2$—CH$_2$—O—, —O—CH$_2$—CH$_2$—,
R3 is $(C_1-C_6)$alkyl, $(C_3-C_6)$alkenyl or —B—(CH$_2$—CH$_2$—O)z—R$_6$ where B is —CH$_2$—O— or —O—,
z is 0, 1 or 2 and R$_6$ is $(C_1-C_4)$alkyl;
$R_4$ is hydrogen or methyl;
$R_5$ is hydrogen or methyl;
x is an integer from 1 to 2
y is 0,1 or 2
with the proviso that
when R3 is —B—(CH$_2$—CH$_2$—O)z—R$_6$, y is 1 and 5-(propargyloxy)-benzo[1,3]dioxole is excluded, as a synergist and a pesticidal active ingredient.

In a preferred embodiment, the composition comprises a compound of Formula (I), wherein x is 1. In a further preferred embodiment y is 1.

In formula (I) $R_1$ and $R_2$, similar or different, denote preferably methyl, ethyl or $R_1O$— and $R_2O$— together represent a group —O—CH$_2$—O— or —O—CH$_2$—CH$_2$—.

$R_3$ is preferably $(C_3-C_6)$alkyl or $(C_3-C_6)$alkenyl and when y is 1, $R_3$ is preferably a group —CH$_2$—O—(CH$_2$—CH$_2$—O)$_2$—C$_4$H$_9$ or a group —O—(CH$_2$—CH$_2$-O)$_2$—C$_4$H$_9$.

$R_4$ is hydrogen and $R_5$ is methyl.

Particularly preferred are compounds wherein R5 is methyl.

Particularly preferred meanings of $R_1$, $R_2$ and $R_3$, independently each other, are the following:

$R_1$ and $R_2$ are methyl or $R_1O$— and $R_2O$— together represent a group —O—CH$_2$—O—

$R_3$ is propyl, 1-propen-3-yl or 2-propen-3-yl, or, when y is 1, a group —O—(CH$_2$—CH$_2$—O)$_2$—C$_4$H$_9$.

Preferred compounds as synergist in the composition according to the present invention are:
5-(but-2-ynyloxy)-benzo[1.3]dioxole
5-(but-2-ynyloxy)-6-propyl-benzo[1.3]dioxole
5-(propargyloxy)-6-propyl-benzo[1.3]dioxole
1-(propargyloxy)-6-propyl-3,4-dimethoxybenzene
1-(but-2-ynyloxy)-3,4-dimethoxybenzene
1-(propargyloxy)-6-propyl-3,4-dimethoxybenzene
1-(but-2-ynyloxy)-6-propyl-3,4-dimethoxybenzene
5-[2-(2-butoxyethoxy)-ethoxy]methyl-6-(but-2-ynyloxy)-benzo[1.3]dioxole
5-(but-2-ynyloxy)-2,3-dihydrobenzofuran
6-(but-2-ynyloxy)-5-propyl-2,3-dihydrobenzofuran.

More preferred compounds are:
5-(but-2-ynyloxy)-benzo[1.3]dioxole
5-(but-2-ynyloxy)-6-propyl-benzo[1.3]dioxole
1-(propargyloxy)-6-propyl-3,4-dimethoxybenzene
1-(but-2-ynyloxy)-6-propyl-3,4-dimethoxybenzene
5-[2-(2-butoxyethoxy)-ethoxy]methyl-6-(but-2-ynyloxy)-benzo[1.3]dioxole
5-(but-2-ynyloxy)-2,3-dihydrobenzofuran
6-(but-2-ynyloxy)-5-propyl-2,3-dihydrobenzofuran.

Still more preferred compounds according to the invention are:
5-(but-2-ynyloxy)-benzo[1.3]dioxole
5-(but-2-ynyloxy)-6-propyl-benzo[1.3]dioxole
5[2-(2-butoxyethoxy)-ethoxy]methyl-6-(but-2-ynyloxy)-benzo[1.3]dioxole
6-(but-2-ynyloxy)-5-propyl-2,3-dihydrobenzofuran.

In a further aspect the invention concerns a process for preparing a compound of Formula (I) comprises the step of reacting a compound of Formula (II) with a compound of Formula (III):

(I)

wherein $R_1, R_2, R_3, R_4, R_5$, x, y have the same meanings as in Formula (I), Z is a halogen atom in the presence of a suitable base and solvent.

Preferably Z is selected from the group consisting of Cl, Br and I.

The preferred solvent used for the reaction includes aliphatic ketone such as acetone, butan-2-one; alkyl or alicyclic ethers such as isopropyl ether, tertbutyl methyl ether, tetrahydrofuran, dioxane; amides such as N, N.dimethylformamide, N,N, dimethylacetamide; cyclic imides such as N-methyl pyrrolidone; sulfoxides such as dimethylsulfoxide; and mixtures thereof The preferred suitable base used for the reaction includes alkaline hydrides such as sodium hydride and potassium hydride; alkaline hydroxides such as sodium hydroxide and potassium hydroxide; alkaline carbonates such as sodium carbonate and potassium carbonate.

The molar ratio of the base with respect to the compound of the Formula (II) is in the range from 1:1 to 5:1. A molar ratio in the range from 2:1 to 1:1 is preferred.

The reaction can be carried out in the co-presence of a suitable alkaline halogenide such as sodium iodide or potassium iodide.

The compound of the Formula (III) is used in the reaction in a molar ratio with respect to the compound of the formula (II) in the range from 5:1 to 1:1. A molar ratio in the range from 2:1 to 1:1 is preferred.

The process according to the invention provides for a preferred reaction temperature in the range from 20° C. to 210° C.; a more preferred range is from 60° to 150° C. The preferred reaction time is from 4 to 24 hours.

After completing the reaction, the compounds of the present invention can be isolated by post reaction treatments. Among these treatments, addition of water to the reaction mixture, extraction with a suitable organic solvent and then concentration and drying under vacuum can be cited. The compounds can be purified with the suitable methods such as crystallizing, distilling or purifying on separation columns.

The compounds of the Formula (II) when y is 0 are commercially available on the market; when y is 1 or 2 they can be obtained by a well know methods in the art such as by acylation of the compounds of the Formula (IV)

(IV)

wherein $R_1$, $R_2$, $R_3$ and y have the same meanings as in Formula (I) and by further oxidation through a Baeyer-Villiger reaction of the suitable ketone derivative, as reported, for example, in EP 1,638,909.

The oxidation is carried out in a suitable solvent, preferably in a chloride solvent such as, for example, dichloromethane, by reacting the suitable ketone compound with an organic acid such as, for example, formic acid or acetic acid, and hydrogen peroxide at temperature in the range from 30° to 60° C., preferably at 40° C.

The acylation reaction is carried out by using the suitable acyl derivative such as, for example, acetic anhydride or acetyl chloride, in net or in a chlorinated solvent such as, for example, methylene chloride or ethylene dichloride, in the presence of a suitable Friedel-Crafts catalyst such as, for example, zinc chloride, iron(II) choride, iron (III) chloride at temperature in the range from 40° to 80° C. as reported, for example, in U.S. Pat. No. 6,342,613.

The compounds of Formula (II), when x is 1, y is 1 and $R_3$ is propyl, can be obtained by Claisen rearrangement of the allyl ether of the compound of Formula (II) when x is 1 and y is zero, in neat under heating and subsequent hydrogenation reaction in the presence of a suitable heterogeneous catalyst such as Pd and Pt on carbon and Raney Ni. The allyl ether can be obtained through a condensation reaction of the compound of Formula (II), commercially available, when x is 1 and y is zero, with a suitable allyl halogenide, such as allyl bromide or chloride, in acetone and in the presence of a suitable inorganic base such as sodium hydroxide, potassium hydroxide, sodium carbonate and potassium carbonate.

The compounds of the Formula (IV) are commercially available on the market or can be obtained by methods known to the expert in the art.

For example, compounds of Formula (IV) can be obtained from the compounds of the Formula (V)

(V)

wherein $R_1$ and $R_2$ have the same meanings as in Formula (I), by reacting the compound of Formula (V) with a suitable acyl derivatives, such as an anhydride or an acylic chloride, and further reducing the obtained compound as reported, for example, in U.S. Pat. No. 6,342,613;

When $R_3$ is $-CH_2-O-(CH_2-CH_2-O)_2-C_4H_9$, the compounds of Formula (IV) can be obtained through chloromethylation reaction of the compounds of Formula (V) and subsequent reaction with butoxydiethylene glycol in the presence of a suitable base. When $R_3$ is $-O-(CH_2-CH_2-O)_2-C_4H_9$, the compounds of the formula (IV) can be obtained by acylation and subsequent Baeyer-Villiger oxidation of the compounds of the Formula (V); the phenol compound so obtained is then reacted with the suitable butoxy diethylene glycol halogenide in the presence of a suitable base.

The pesticidal composition of the present invention includes a compound of Formula (I) and a pesticidal active ingredient. The ratio between the present compound and the pesticidal active ingredient which are contained in the pesticidal composition of the present invention is optionally adjustable without limitation according to the control objectives such as kinds of pests, places for application, timings of applying, kinds of the pesticidal active ingredient; typical weight ratio (the present compound: pesticidal active ingredient) being from about 1:100 to about 100:1, preferably from about 1:50 to about 50:1, more preferably 20:1 to 1:1.

Examples of the pesticidal active ingredient contained the pesticidal composition of the present invention together with the present compound are on or a mixture of the following:

pyrethroid compounds such as allethrin, tetramethrin, prallethrin, phenothrin, resmethrin, cyphenothrin, permethrin, cypermethrin, alpha-cypermethrin, zeta-cypermethrin, deltamethrin, tralomethrin, cyfluthrin, beta-cyfluthrin, cyhalothrin, lambda-cyhalothrin, flumethrin, imiprothrin, etofenprox, fenvalerate, esfenvalerate, fenpropathrin, silafluofen, bifenthrin, transfluthrin, flucythrinate, tau-fluvalinate, acrinathrin, tefluthrin, cyprothrin, 2,3,5,6-tetrafluoro-4-(methoxymethyl)benzyl (EZ)-(1RS,3RS;1RS,3S R)-2,2-dimethyl-3-prop-1-enylcyclopropane carboxylate, 2,3,5,6-tetrafluoro-4-methylbenzyl(EZ)-(1RS,3RS;1RS,3SR)-2,2-dimethyl-3-p-rop-1-enylcyclopropane carboxylate, 2,3,5,6-tetrafluoro-4-(methoxymethyl)benzyl(1RS,3RS;1RS,3SR)-2,2-dimethyl-3-(2-methylprop-1-enyl)cyclopropanecarboxylate, empenthrin, 2,3,5,6-tetrafluoro-4-methoxymethylbenzyl(EZ)-(1RS,3RS;1RS,3SR)-3-(2-cyan-o-1-propenyl)-2,2-dimethylcyclopropanecarboxylate, 2,3,5,6-tetrafluoro-4-methoxymethyl benzyl (EZ)-(1RS,3 RS;1RS,3SR)-3-(2-cyano-2-ethoxycarbonylvinyl)-2,2-dimethylcyclopropanecarboxylate, 2,3,5,6-tetrafluoro-4-methoxymethylbenzyl(1RS,3RS;1RS,3SR)-3-(2,2-dichlorovinyl)-2,2-dimethylcycl opropanecarboxylate, 2,3,5,6-tetrafluoro-4-methoxymethyl benzyl (EZ)-(1RS,3RS;1RS,3SR)-3-methoxy-iminomethyl-2,2-dimethylcyclopropanecarboxylate and 2,3,5,6-tetrafluoro-4-methoxymethylbenzyl(EZ)-(1RS,3RS;1RS,3S R)-3-(2-ethoxycarbonyl-2-fluorovinyl)-2,2-dimethylcyclopropanecarboxylate;

Organic phosphorus compounds such as dichlorvos, fenitrothion, cyanophos, profenofos, sulprofos, phenthoate, isoxathion, tetrachlorvinphos, fenthion, chlorpyriphos, diazinon, acephate, terbufos, phorate, chlorethoxyfos, fosthiazate, ethoprophos, cadusafos and methidathion;

carbamate compounds such as propoxur, carbaryl, metoxadiazone, fenobucarb, methomyl, thiodicarb, alanycarb, benfuracarb, oxamyl, aldicarb and methiocarb;benzoylphenylurea compounds such as lufenuron, chlorfluazuron, hexaflumuron, diflubenzuron, triflumuron, teflubenzuron, flufenoxuron, fluazuron, novaluron, triazuron and bistrifluron; juvenile hormone-like substances such as pyriproxyfen, methoprene, hydroprene and fenoxycarb;

neonicotinoid compounds such as acetamiprid, nitenpyram, thiacloprid, thiamethoxam, dinotefuran, imidacloprid and clothianidin;

phenylpyrazole compounds such as acetoprole and ethiprole;

benzoylhydrazine compounds such as tebufenozide, chromafenozide, methoxyfenozide and halofenozide;

other pesticidal active ingredients such as diafenthiuron, pymetrozine, flonicamid, triazamate, buprofezin, spinosad, emamectin benzoate, chlorfenapyr, indoxacarb MP, pyridalyl, cyromazine, fenpyroximate, tebufenpyrad, tolfenpyrad, pyridaben, pyrimidifen, fluacrypyrim, etoxazole, fenazaquin, acequinocyl, hexythiazox, clofentezine, fenbutatin oxide, dicofol, propargite, abamectin, milbemectin, amitraz, cartap, bensultap, thiocyclam, endosulfan, spirodiclofen, spiromesifen, amidoflumet and azadirachtin.

One kind or two or more kinds of these pesticidal active ingredients may be used for the pesticidal composition of the present invention.

In another aspect the present invention concerns a pesticidal formulation comprises the composition of the present invention and an inert carrier. Such carrier can be a solid carrier, a liquid carrier and/or a gaseous carrier. The pesticidal formulation may further comprise a surfactant and other adjuvants. The pesticidal formulation can also comprises other synergists in order to enlarge the action spectrum.

Such a pesticidal final formulation can be in the form of, for example, an emulsion, an oil solution, a shampoo preparation, a flowable preparation, a powder, a wettable powder, a granule, a paste, a microcapsule, a foam, an aerosol, a carbon dioxide gas preparation, a tablet, a resin preparation, a paper preparation, a nonwoven fabric preparation, and a knitted or woven fabric preparation. These final formulation may be used in the form of a poison bait, a pesticide coil, an electric pesticide mat, a smoking preparation, a fumigant, or a sheet. The pesticidal formulation of the present invention contains from 0.01 to 98% by weight of the present pesticidal composition. A solid carrier used for formulation includes finely-divided powder or granules of clay (e.g. kaolin clay, diatomaceous earth, bentonite, Fubasami clay, acid clay, etc.), synthetic hydrated silicon oxide, talc, ceramics, other inorganic minerals (e.g., sericite, quartz, sulfur, activated carbon, calcium carbonate, hydrated silica, etc.) or chemical fertilizers (e.g., ammonium sulfate, ammonium phosphate, ammonium nitrate, ammonium chloride, urea, etc.); a substance which can be sublimated and is in the solid form at room temperature (e.g., 2,4,6-triisopropyl-1,3,5-trioxane, naphthalene, p-dichlorobenzene, camphor, adamantan, etc.); wool; silk; cotton; hemp; pulp; synthetic resins (e.g., polyethylene resins such as low-density polyethylene, straight low-density polyethylene and high-density polyethylene; ethylene-vinyl ester copolymers such as ethylene-vinyl acetate copolymers; ethylene-methacrylic acid ester copolymers such as ethylene-methyl methacrylate copolymers and ethylene-ethyl methacrylate copolymers; ethylene-acrylic acid ester copolymers such as ethylene-methyl acrylate copolymers and ethylene-ethyl acrylate copolymers; ethylene-vinylcarboxylic acid copolymers such as ethylene-acrylic acid copolymers; ethylene-tetracyclododecene copolymers; polypropylene resins such as propylene homopolymers and propylene-ethylene copolymers; poly-4-methylpentene-1, polybutene-1, polybutadiene, polystyrene; acrylonitrile-styrene resins; styrene elastomers such as acrylonitrile-butadiene-styrene resins, styrene-conjugated diene block copolymers, and styrene-conjugated diene block copolymer hydrides; fluororesins; acrylic resins such as poly(methyl methacrylate); polyamide resins such as nylon 6 and nylon 66; polyester resins such as polyethylene terephthalate, polyethylene naphthalate, polybutylene terephthalate, and polycyclohexylenedimethylene terephthalate; polycarbonates, polyacetals, polyacrylsulfones, polyarylates, hydroxybenzoic acid polyesters, polyetherimides, polyester carbonates, polyphenylene ether resins, polyvinyl chloride, polyvinylidene chloride, polyurethane, and porous resins such as foamed polyurethane, foamed polypropylene, or foamed ethylene, etc.), glasses, metals, ceramics, fibers, cloths, knitted fabrics, sheets, papers, yarn, foam, porous substances, and multifilaments. A liquid carrier includes, for example, aromatic or aliphatic hydrocarbons (e.g., xylene, toluene, alkylnaphthalene, phenylxylylethane, kerosine, gas oil, hexane, cyclohexane, etc.), halogenated hydrocarbons (e.g., chlorobenzene, dichloromethane, dichloroethane, trichloroethane, etc.), alcohols (e.g., methanol, ethanol, isopropyl alcohol, butanol, hexanol, benzyl alcohol, ethylene glycol, etc.), ethers (e.g., diethyl ether, ethylene glycol dimethyl ether, diethylene glycol monomethyl ether, diethylene glycol monoethyl ether, propylene glycol monomethyl ether, tetrahydrofuran, dioxane, etc.), esters (e.g., ethyl acetate, butyl acetate, etc.), ketones (e.g., acetone, methyl ethyl ketone, methyl isobutyl ketone, cyclohexanone, etc.), nitriles (e.g., acetonitrile, isobutyronitrile, etc.), sulfoxides (e.g., dimethyl sulfoxide, etc.), amides (e.g., N,N-dimethylformamide, N,N-dimethylacetamide, cyclic imides (e.g. N-methylpyrrolidone) alkylidene carbonates (e.g., propylene carbonate, etc.), vegetable oil (e.g., soybean oil, cottonseed oil, etc.), vegetable essential oils (e.g., orange oil, hyssop oil, lemon oil, etc.), and water.

A gaseous carrier includes, for example, butane gas, flon gas, liquefied petroleum gas (LPG), dimethyl ether, and carbon dioxide gas.

Among the surfactants included in the pesticidal formulation of the invention alkyl sulfate ester salts, alkyl sulfonates, alkyl aryl sulfonates, alkyl aryl ethers and polyoxyethylenated products thereof, polyethylene glycol ethers, polyvalent alcohol esters and sugar alcohol derivatives can be cited.

Among other adjuvants included in the pesticidal formulation binders, dispersants and stabilizers, specifically, for example, casein, gelatin, polysaccharides (e.g., starch, gum arabic, cellulose derivatives, alginic acid, etc.), lignin derivatives, bentonite, sugars, synthetic water-soluble polymers (e.g., polyvinyl alcohol, polyvinylpyrrolidone, polyacrylic acid, etc.), PAP (acidic isopropyl phosphate), BHT (2,6-di-t-butyl-4-methylphenol), BHA (a mixture of 2-t-butyl-4-methoxyphenol and 3-t-butyl-4-methoxyphenol), vegetable oils, mineral oils, fatty acids and fatty acid esters can be cited.

Other synergists can be represented by piperonyl butoxide, MGK 264 and Verbutin. A base material for a resin preparation includes, for example, polyethylene resins such as low-density polyethylene, straight low-density polyethylene and high-density polyethylene; ethylene-vinyl ester copolymers such an ethylene-vinyl acetate copolymers; ethylene-methacrylic acid ester copolymers such as ethylene-methyl methacrylate copolymers and ethylene-ethyl methacrylate copolymers; ethylene-acrylic acid ester copolymers such as ethylene-methyl acrylate copolymers and ethylene-ethyl acrylate copolymers; ethylene-vinylcarboxylic acid copolymers such as ethylene-acrylic acid copolymers; ethylene-tetracyclododecene copolymers; polypropylene resins such as propylene copolymers and propylene-ethylene copolymers; poly-4-methylpentene-1, polybutene-1, polybutadiene, polystyrene, acrylonitrile-styrene resins; styrene elastomers such as acrylonitrile-butadiene-styrene resins, styrene-conjugated diene copolymers, and styrene-conjugated diene block copolymer hydrides; fluororesins; acrylic acid resins such as poly(methyl methacrylate); polyamide resins such as nylon 6 and nylon 66; polyester resins such as polyethylene terephthalate, polyethylene naphthalate, polybutylene butalate, and polycylohexylenedimethylene terephthalate; polycarbonates, polyacetals, polyacrylsulfones, polyarylate, hydroxybenzoic acid polyesters, polyetherimides, polyester carbonates, polyphenylene ether resins, polyvinyl chloride, polyvinylidene chloride, and polyurethane. These base materials may be used alone or as a mixture of two or more. A plasticizer such as phthalic acid ester (e.g., dimethyl phthalate, dioctyl phthalate, etc.), adipic acid ester or stearic acid may be added to these base materials, if necessary.

The resin preparation can be obtained by kneading the present pesticidal composition into the base material, followed by molding such as injection molding, extrusion molding or press molding. The resulting resin preparation may be formed into the shape of a plate, a film, a tape, a net, a string or the like via a further step of molding, cutting, or the like, if necessary. These resin preparations may be used in the form of an animal collar, an animal ear tag, a sheet preparation, a lead, or a horticultural post. A base material of a poison bait includes, for example, cereal powder, vegetable oil, sugar and crystalline cellulose. An antioxidant such as dibutylhydroxytoluene or nordihydroguaiaretic acid, a preservative such as dehydroacetic acid, an agent for preventing children or pets from erroneously eating such as hot pepper powder, and a pest-attractive perfume such as cheese perfume, onion perfume or peanut oil may be added to the base material, if necessary.

The present compound can be used in pest control by applying an effective amount of the present pesticidal composition to pests directly and/or a biotope thereof (e.g., plants, animals, soil, etc.).

When the pesticidal composition of the present invention is used for controlling pests in agriculture and forestry, the application amount is preferably in the range from 1 to 100,000 g/ha, more preferably from 10 to 1,000 g/ha of total amount of the present composition. When the pesticidal composition of the present invention is finally formulate in the form of an emulsion, a wettable powder, a flowable agent, or a microcapsule, it is preferably used after dilution with water so as to have the present composition concentration of 0.01 to 1,000 ppm. When the pesticidal composition of the present invention is formulated in the form of an oil solution, a powder or a granule, it is preferably used as it is.

These final formulations as they are may be sprayed as they are to plants to be protected from pests, or may be diluted with water and then sprayed to a plant to be protected from pests. Soil can be treated with these final formulations to control pests living in the soil. Seedbeds before planting or planting holes or plant feet in planting can be also treated with these preparations. Further, a sheet preparation of the pesticidal composition of the present invention may be applied by winding around plants, disposing in the vicinity of plants, laying on the soil surface at the plant feet, or the like.

When the pesticidal composition of the present invention is used for controlling epidemic pests, the application amount is preferably from 0.001 to 100 mg/m$^3$ of total amount of the pesticidal composition for application to space, and 0.001 to 1,000 mg/m$^2$ of total amount of the pesticidal composition for application to a plane. When the pesticidal composition of the present invention is the form of an emulsion, a wettable powder or a flowable agent, it is preferably applied after dilution with water so as to have the present pesticidal composition concentration of 0.001 to 100,000 ppm, more preferably 0.01 to 1,000 ppm. When the pesticidal composition of the present invention is the form of an oil solution, an aerosol, a smoking preparation or a poison bait, it is preferably applied as it is. The pesticidal composition in the form of pesticide coil, or an electric pesticide mat is applied by emitting the present pesticidal composition by heating depending on its form. The pesticidal composition in the form of a resin preparation, a paper preparation, a tablet, a nonwoven fabric preparation, a knitted or woven fabric preparation or a sheet preparation can be applied, for example, by leaving the preparation as it is in a space to be applied and by sending air to the preparation.

A space to which the pesticidal composition of the present invention is applied for prevention of epidemics includes, for example, a closet, a Japanese-style closet, a Japanese-style chest, a cupboard, a lavatory, a bathroom, a lumber room, a living room, a dining room, a warehouse, and the car inside. The pesticidal composition may be also applied in outdoor open space. When the pesticidal composition of the present invention is used for controlling parasites living outside of a livestock such as a cow, a horse, a pig, a sheep, a goat or a chicken, or a small animal such as a dog, a cat, a rat or a mouse, it can be used for said animal by a known method in the veterinary field. Specifically, when systemic control is intended, the pesticidal composition is administered, for example, as a tablet, a mixture with feed, a suppository or an injection (e.g., intramuscularly, subcutaneously, intravenously, intraperitoneally, etc.). When non-systemic control is intended, a method of using the pesticidal composition of the present invention includes spraying, pour-on treatment or a spot-on treatment with the pesticidal composition in the form of an oil solution or an aqueous liquid, washing an animal with the pesticidal composition in the form of a shampoo preparation, and attachment of a collar or a ear tag made of the pesticidal composition in the form of a resin preparation to an animal. When administered to an animal, total amount of the present active ingredient is usually in the range of 0.01 to 1,000 mg per 1 kg body weight of the animal.

Pests against which the pesticidal composition of the present invention has controlling effect include harmful arthropods such as insects and mites. More specifically, examples thereof are listed below.

Hemiptera:
Delphacidae such as *Laodelphax striatellus, Nilaparvata lugens, Sogatella furcifera* and the like,
Deltocephalidae such as *Nephotettix cincticeps, Nephotettix virescens* and the like, Aphididae such as *Aphis gossypii, Myzus persicae* and the like,
Pentatomidae and Alydidae, such as *Nezara antennata, Riptortus clavetus, Eysarcoris lewisi, Eysarcoris parvus, Plautia stali, Halyomorpha mista* and the like, Aleyrodidae such as *Trialeurodes vaporariorum, Bemisia argentifolii* and the like, Diaspididae, Coccidae and Margarodidae, such as *Aonidiella aurantii, Comstockaspis perniciosa, Unaspis citri, Ceroplastes rubens, Icerya purchasi* and the like, Tingidae, Cimicidae such as *Cimex lectularius* and the like, Psyllidae, and the like; Lepidoptera: Pyralidae such as *Chilo suppressalis, Cnaphalocrocis medinalis, Notarcha derogata, Plodia interpunctella* and the like, Noctuidae such as *Spodoptera litura, Pseudaletia separata, Trichoplusia* spp., *Heliothis* spp., *Helicoverpa* spp. and the like, Pieridae such as *Pieris rapae* and the like, Tortricidae such as *Adoxophyes* spp., *Grapholita molesta, Cydia pomonella* and the like, Carposinidae such as *Carposina niponensis* and the like, Lyonetiidae such as *Lyonetia* spp. and the like, Lymantriidae such as *Lymantria* spp., *Euproctis* spp. and the like, Yponomeutidae such as *Plutella xylostella* and the like, Gelechiidae such as *Pectinophora gossypiella* and the like, Arctiidae such as *Hyphantria cunea* and the like, Tineidae such as *Tinea translucens, Tineola bisselliella* and the like; Diptera: Culicidae such as *Culex pipiens pallens, Culex tritaeniorhynchus, Culex quinquefasciatus* and the like, *Aedes* spp. such as *Aedes aegypti, Aedes albopictus* and the like, *Anopheles* spp. such as *Anopheles sinensis* and the like, Chironomidae, Muscidae such as *Musca domestica, Muscina stabulans* and the like, Calliphoridae, Sarcophagidae, Fanniidae, Anthomyiidae such as *Delia platura, Delia antiqua* and the like, Tephritidae, Drosophilidae, Phoridae such as *Megaselia spiracularis* and the like, Psychodidae such as *Clogmia albipunctata* and the like, Simuliidae, Tabanidae, *Stomoxys* spp., Agromyzidae, and the like; Coleoptera: Corn rootworms such as *Diabrotica virgifera virgifera, Diabrotica undecimpunctata howardi* and the like, Scarabaeidae such as *Anomala cuprea, Anomala rufocuprea* and the like, Rhynchophoridae, Curculionidae and Bruchidae, such as *Sitophilus zeamais, Lissorhoptrus oryzophilus, Callosobruchus chienensis* and the like, Tenebrionidae such as *Tenebrio molitor, Tribolium castaneum* and the like, Chrysomelidae such as *Oulema oryzae, Aulacophora femoralis, Phyllotreta striolata, Leptinotarsa decemlineata* and the like, Dermestidae such as *Dermestes maculates* and the like, Anobiidae, *Epilachna* spp. such as *Epilachna vigintioctopunctata* and the like, Lyctidae, Bostrychidae, Ptinidae, Cerambycidae, *Paederus fuscipes*, and the like; Blattaria: *Blattella germanica, Periplaneta fuliginosa, Periplaneta americana, Periplaneta brunnea, Blatta orientalis* and the like; Thysanoptera: *Thrips palmi, Thrips tabaci, Frankliniella occidentalis, Frankliniella intonsa* and the like; Hymenoptera: Formicidae such as *Monomorium pharaosis, Formica fusca japonica, Ochetellus glaber, Pristomyrmex pungens, Pheidole noda*, and the like; Vespidae, Bethylidae, Tenthredinidae such as *Athalia japonica*, and the like; Orthoptera: Gryllotalpidae, Acrididae, and the like; Aphaniptera: *Ctenocephalides felis, Ctenocephalides canis, Pulex irritans, Xenopsylla cheopis*, and the like; Anoplura: *Pediculus humanus corporis, Phthirus pubis, Haematopinus eurysternus, Dalmalinia ovis*, and the like; Isoptera: Subterranean termites such as *Reticulitermes speratus, Coptotermes formosanus, Reticulitermes flavipes, Reticulitermes hesperus, Reticulitermes virginicus, Reticulitermes tibialis, Heterotermes aureus*, and the like, Dry wood termites such as Incisitermes minor, and the like, Damp wood termites such as *Zootermopsis nevadensis*, and the like; Acarina: Tetranychidae such as *Tetranychus urticae, Tetranychus kanzawai, Panonychus citri, Panonychus ulmi, Oligonychus* spp. and the like, Eriophyidae such as *Aculops pelekassi, Aculus schlechtendali*, and the like, Tarsonemidae such as *Polyphagotarsonemus latus*, and the like, Tenuipalpidae, Tuckerellidae, Ixodidae such as *Haemaphysalis longicornis, Haemaphysalis flava, Dermacentor variabilis, Ixodes ovatus, Ixodes persulcatus, Ixodes scapularis, Boophilus microplus, Amblyomma americanum, Rhipicephalus sanguineus*, and the like, Acaridae such as *Tyrophagus putrescentiae*, and the like, Epidermoptidae such as *Dermatophagoides farinae, Dermatophagoides ptrenyssnus*, and the like, Cheyletidae such as *Cheyletus eruditus, Cheyletus malaccensis, Cheyletus moorei, Ornithoonyssus bacoti, Ornithonyssus sylvairum* and the like, Dermanyssidae such as *Dermanyssus gallinae*, and the like, Trombiculidae such as *Leptotrombidium akamushi*, and the like; Araneae: *Chiracanthium japonicum, Latrodectus hasseltii*, and the like; Chilopoda: *Thereuonema hilgendorfi, Scolopendra subspinipes*, and the like; Diplopoda: *Oxidus gracilis, Nedyopus tambanus*, and the like; Isopoda: *Armadillidium vulgare*, and the like; Gastropoda: *Limax marginatus, Limax flavus*, and the like.

The present invention will be detailed by the following Examples given for illustrating and non limiting purposes.

EXAMPLES

Example 1

Comparative Example of a Product Described in U.S. Pat. No. 3,423,428

Synthesis of 5-(propargyloxy)-benzo[1,3]dioxole

A mixture of 12.9 g (0.092 moles) of 5-hydroxy-benzo[1.3]dioxole, 13.0 g (0.092 moles) of anhydrous potassium carbonate in ml 30 of acetone was added with 13.7 g (0.092 moles) of a solution of propargyl bromide in toluene (80% w/w) and the mixture was heated to reflux for 4 hrs. The mixture was then cooled to room temperature, filtered and the filtrate evaporated u.v (20 ° C./ 21 mbar). The residue was purified on silica gel column (eluant n-hexane: isopropyl ether 95: 5 v/v). A liquid product (13.6 g, 95.6% purity) was obtained whose NMR and MS analyses correspond to those of the aforementioned compound is obtained.

$^1$H NMR (400 MHz; CDCl$_3$): δ: 2.53 (t, 1H, J=2.4 Hz); 4.605 (d, 2H, J=2.4 Hz); 5.91 (s, 2H); 6.41 (dd, 1H, Jo=8.8 Hz, Jm=2.8 Hz); 6.56 (d, 1H, Jm=2.8 Hz); 6.71 (d, 1H, Jo=8.8 Hz).

$^{13}$C NMR (100MHz; CDCl$_3$): δ: 56.72 (CH$_2$); 75.42 (CH); 78.61 (Cq); 98.57 (CH); 101.15 (CH$_2$); 106.34 (CH); 107.77 (CH); 142.25 (Cq); 148.13 (Cq); 152.86 (Cq).

Example 2

Synthesis of 5-(but-2-ynyloxy)-benzo[1.3]dioxole

A mixture of 7.0 g (0.05 moles) of 5-hydroxy-benzo[1.3]dioxole, 6.91 g (0.05 moles) of anhydrous potassium carbonate in ml 25 of acetone was added with 6.65 g (0.05 moles) of 1-bromo-2-butyne. The mixture was heated to reflux for 6 hrs. The mixture was then cooled to room temperature, filtered and the filtrate evaporated u.v (20° C./21 mbar). The residue was then purified on silica gel column (eluant n-hexane: ethyl acetate 3:1 v/v). A liquid product (6.1 g, 95% purity) was obtained whose NMR and MS analyses correspond to those of the aforementioned compound.

LC-ESI-MS m/z 191.1 [(M+H)$^+$, 29%], 133.1 (55%), 139.1 (64%), 151 (100%), 161.1 (56%).

$^1$H NMR (400 MHz; CDCl$_3$): δ: 1.85 (t, 3H, J=2.4 Hz); 4.55 (q, 2H, J=2.4 Hz); 5.90 (s, 2H); 6.39 (dd, 1H, Jo=8.6 Hz, Jm=2.6 Hz); 6.56 (d, 1H, Jm=2.6 Hz); 6.70 (d, 1H, Jo=8.6 Hz).

$^{13}$C NMR (100MHz; CDCl$_3$): δ: 19.16, 57.28, 74.05, 83.57, 98.40, 100.99, 106.17, 107.77, 141.96, 148.10, 153.22.

Example 3A

Synthesis of 5-(but-2-ynyloxy)-6-propyl-benzo[1.3]dioxole a) Synthesis of 5-acetyl-6-propyl-benzo[1.3]dioxole A mixture of 16.75 g (0.1 mole) of 5-propyl-benzo[1.3.]dioxole (purity 98% w/w) and 5.13 g (0.05 moles) of acetic anhydride was added with 0.7 g (5 mmoles) of anhydrous zinc chloride.

The mixture was heated to 90°-100° C. for 6 hrs, cooled to room temperature and, then, added with 40 ml of water and 40 ml of dichloromethane. The organic phase was separated and the aqueous phase was extracted twice with dichloromethane (2× 30 ml). The organic phases were collected together, and washed with 30 ml of a saturated aqueous solution of sodium carbonate. The organic phase was separated, evaporated u.v. (20° C./21 mbar) and the residue distilled at 113-115° C./1 mbar, obtaining 8.0 g (0.035 moles) of 5-acetoxy-6-propyl-benzo[1.3]dioxole that, after some time, crystallized with m.p. 33°-34° C.

GC-MS: m/z 206 (M$^+$, 34%), 177 (31%), 191 (100%).

$^1$H NMR (400 MHz; CDCl$_3$): δ: 0.95 (t, 3H, J=7.5 Hz); 1.56 (m, 2H, J=7.5 Hz); 2.51 (s, 3H); 2.78 (t, 2H, J=7.5 Hz); 5.98 (s, 2H); 6.71 (s, 1H); 7.14 (s, 1H).

$^{13}$C-NMR (CDCl$_3$, 100MHz) δ14.28, 25.19, 29.97, 36.48, 101.76, 109.57, 111.28, 131.16, 139.85, 145.56, 150.09, 199.96.

b) Synthesis of 5-hydroxy-6-propyl-benzo[1.3]dioxole

The product was then added to 13 ml of dichloromethane and to 6.72 g (0.14 moles) of formic acid (95% w/w): the mixture was heated to reflux and 20.2 g (0.208 moles) of hydrogen peroxide (35% w/w) were added dropwise.

The mixture was then cooled to room temperature and the organic phase was separated and the aqueous phase was extracted twice with dichloromethane (2× 20 ml). The organic phases were collected and washed with 30 ml of a saturated aqueous solution of sodium carbonate. The solution was evaporated u.v (20° C./21 mbar) and the residue was dissolved in an aqueous solution (20% w/w) of sodium hydroxide (g.6.5)

The aqueous mixture was then stirred at room temperature for 1 hr and was washed with 5 ml of dichloromethane. After separation of the organic phase, the aqueous solution was acidified with aqueous HCl until acid pH (1-1.5) and then extracted twice with 10 ml of dichloromethane, being the organic phases collected and dried on sodium sulphate. After evaporation of the organic solution u.v. (20° C./21 mbar) the residue was distilled at 104-112° C. /0.1 mbar to give 6.1 g of a product that, after crystallisation (isopropyl ether) gave 5.2 g of a white solid product with m.p. 68°-70° C. and whose NMR and MS analyses correspond to those of the aforementioned compound.

GC-MS: m/z 180 (M+, 30%), 151 (100%).

$^1$H NMR (400 MHz; CDCl$_3$): δ: 0.95 (t, 3H, J=7.3 Hz); 1.59 (m, 2H, J=7.3 Hz); 2.47 (t, 2H, J=7.3 Hz); 4.63 (s, 1H, OH); 5.86 (s, 2H); 6.38 (s, 1H); 6.59 (s, 1H).

$^{13}$C-NMR (CDCl3, 100MHz) δ13.81, 23.14, 31.77, 98.10, 100.81, 109.32, 120.13, 141.25, 145.85, 147.62.

c) Synthesis of 5-(but-2-ynyloxy)-6-propyl-benzo[1.3]dioxole

Following the same procedure as in Example 2, 3.65 g (0.02 moles) of 5-hydroxy-6-propyl-benzo[1.3]dioxole were reacted with 2.7 g (0.02 moles) of 1-bromo-2-butyne and 2.8 g (0.02 moles) of anhydrous potassium carbonate in 15 ml of acetone. After the work up of the reaction as in Example 2, a residue was obtained that after distillation at 115-117° C./0.2 mbar gave 3.9 g of a liquid product that, after some time, crystallized with m.p. 39° -40 ° C. and whose NMR and MS analyses correspond to those of the aforementioned compound.

GC-MS: m/z 232 (M$^+$, 56%), 151 (52%), 179 (100%).

$^1$H NMR (400 MHz; CDCl$_3$): δ: 0.93 (t, 3H, J=7.5 Hz); 1.55 (m, 2H, J=7.5 Hz); 1.85 (t, 3H , J=2.4 Hz); 2.51 (t, 2H J=7.5 Hz); 4.56 (q, 2H, J=2.4 Hz); 5.88 (s, 2H); 6.63 (s, 1H); 6.64 (s, 1H).

$^{13}$C-NMR (100MHz, CDCl$_3$): δ: 3.54, 13.82, 23.35, 31.83, 57.98, 74.47, 83.21, 96.84, 100.79, 109.39, 124.38, 141.39, 145.55, 150.32.

Example 3B

Alternative synthesis of 5-hydroxy-6-propyl-benzo[1.3]dioxole using 5-hydroxy-benzo[1.3]dioxole (sesamol) as starting material.

A mixture of 50 g (0.36 moles) of 5-hydroxy-benzo[1.3]dioxole, 50 g (0.36 moles) of anhydrous potassium carbonate in ml 250 of acetone was added with 43.5 g (0.36 moles) of allyl bromide. The mixture was heated to reflux for 6 hrs, then cooled to room temperature and filtered.

The filtrate was evaporated u.v. (20° C./21 mbar) and 64.2 g of crude product were obtained, as an orange-brown liquid (5-(allyloxy)benzo[1,3]dioxole).

Claisen rearrangement: without further purification, the crude was stirred for 2 hrs at 170 ° C., then cooled to room temperature: 62.3 g of 6-allylbenzo[1,3]dioxol-5-ol were obtained.

Hydrogenation: the crude melted product was charged to an autoclave and diluted with 100 mL of isopropyl alcohol. 1.55 g of 5% Pd/C were added, and after flushing with nitrogen, the hydrogenation was carried out at 65° C. and 6 bar of $H_2$ for 6 hrs. The mixture was cooled to room temperature and filtered on a celite pad to remove the catalyst. The organic solution was evaporated u.v. (20° C./21 mbar) and the residue distilled at 104°-112° C./0.1 mbar. 61 g of 5-hydroxy-6-propyl benzo[1.3]dioxole were obtained. Following the same procedure as in Example 3 c), 61 g. of 5-hydroxy-6-propyl benzo[1.3]dioxole were reacted with 45.9 g (0.34 moles) of 1-bromo-2-butyne and 47.7 g (0.34 moles) of anhydrous potassium carbonate in 250 ml of acetone. The filtrate in evaporated u.v. (20° C./ 21 mbar) and 69.1 g of 5-(but-2-ynyloxy)-6-propyl-benzo[1.3]dioxole were obtained (purity 75.5%).

The product was purified following the same procedure as in Example 3 b).

Example 4

Synthesis of 5-(propargyloxy)-6-propyl-benzo[1.3]dioxole

Following the same procedure as in Example 3 a) and b), but using 7.2 g (0.04 moles) of 5-hydroxy-6-propyl-benzo[1.3]dioxole, 5.92 g (0.04 moles) of anhydrous potassium carbonate in 40 ml of acetone were reacted with 5.95 g (0.04 moles) of a solution of propargyl bromide in toluene, (80% w/w).

After the work up as in Example 3 c) 6.11 g of a solid product (m.p. 46-48° C.) were obtained whose NMR and MS analyses corresponded to those of the aforementioned compound.

GC-MS: m/z 218 ($M^+$, 56%), 151 (52%), 179 (100%).

$^1$H NMR (400 MHz; $CDCl_3$): 0.93 (t, 3H, J=7.6 Hz); 1.56 (sest, 2H, J=7.6 Hz); 2.50 (t, 1H, J=2.4 Hz); 2.52 (t, 2H, J=7.6 Hz); 4.605 (d, 2H, J=2.4 Hz); 5.90 (s, 2H); 6.64 (s, 1H); 6.65 (s, 1H).

$^{13}$C NMR (100MHz; $CDCl_3$): 13.90 ($CH_3$); 23.47 ($CH_2$); 31.92 ($CH_2$); 57.46 ($CH_2$); 75.20 (CH); 79.061 (Cq); 96.93 (CH); 100.96 ($CH_2$); 109.59 (CH); 124.69 (Cq; 141.78 (Cq; 145.67 (Cq,); 150.05 (Cq,).

Example 5

Synthesis of 1-(propargyloxy)-3,4-dimethoxybenzene

Following the same procedure as in Example 1, 13.8 g (0.1 mole) of 1-hydroxy-3,4-dimethoxybenzene, 13.8 g (0.1 mole) of anhydrous potassium carbonate in ml 50 of acetone and 14.9 g (0.1 mole) of a solution of propargyl bromide in toluene (80% w/w) were reacted. After work up and evaporation of the mixture u.v. (25° C./21 mbar) a residue was obtained that was purified on silica gel column (eluant n-hexane:ethyl acetate 5:1 v/v). A thick oil that after some time solidified with low melting point (28-30° C.) (b.p.: 109-110° C./ 3 mbar) was obtained whose NMR and MS analyses corresponded to those of the aforementioned compound.

$^1$H NMR (400 MHz; $CDCl_3$): δ: 2.51 (t, 1H, J=2,4 Hz); 3.819 (s, 3H); 3.836 (s, 3H); 4.627 (d, 2H, J=2,4 Hz); 6.69 (dd, 1H, Jo=8.8 Hz, Jm=2.2 Hz); 6.79 (d, 1H, Jm=2.2 Hz); 6.72 (d, 1 H, Jo=8.8 Hz).

$^{13}$C NMR (100 MHz; $CDCl_3$): δ: 55.76 ($CH_3$); 56.28 ($CH_3$); 56.37 ($CH_2$); 75.29 (CH); 76.68 (Cq); 101.32 (CH); 104.34 (CH); 111.51 (CH); 144.08 (Cq); 149.77 (Cq); 152.03 (Cq).

Example 6

Synthesis of 1-(but-2-ynyloxy)-3,4-dimethoxybenzene

Following the same procedure as in Example 2, 15.4 g (0.1 mole) of 1-hydroxy-3,4-dimethoxybenzene, 13.8 g (0.1mole) of anhydrous potassium carbonate in ml 50 of acetone and 13.3 g (0.1 mole) of 1-bromo-2-butyne were reacted. After work up and evaporation of the mixture u.v. (20° C./21 mbar), a residue was obtained, that after purification on silica gel column (eluant n-hexane:ethyl acetate 5:1 v/v) gave a thick oil that after some time solidified with low melting point (28-30° C.), whose NMR and MS analyses corresponded to those of the aforementioned compound.

$^1$H NMR (400 MHz; $CDCl_3$): δ: 1.812 (t, 3H, J=2,4 Hz); 3.801 (s, 3H); 3.827 (s, 3H); 4.565 (q, 2H, J=2,4 Hz); 6.6385 (dd, 1 H, Jo=8.8 Hz, Jm=2.8 Hz); 6.557 (d, 1 H, Jm=2.8 Hz); 6.750 (d, 1 H, Jo=8.8 Hz).

$^{13}$C NMR (100MHz; $CDCl_3$): δ: 3.540 ($CH_3$); 55.683 e 56.240 (2 $CH_3$); 56.857 ($CH_2$); 74.101 (Cq); 83.430 (Cq); 101.161 (CH); 104.124 (CH); 111.530 (CH); 143.760 (Cq); 149.678 (Cq); 152.293 (Cq).

Example 7

Synthesis of 1-(propargyloxy)-6-propyl-3,4-dimethoxybenzene a) Synthesis of 1-acetyl-6-propyl-3,4-dimethoxybenzene

Following the same procedure as in Example 3 a), a mixture of 18.02 g (0.1 mole) of 4-propyl-1.2-dimethoxybenzene, 5.13 g (0.05 moles) of acetic anhydride and 0.7 g (5 mmoles) of anhydrous zinc chloride was reacted at 80-90° C. for 6 hrs. After washing, separation of the organic phase and evaporation u.v (20° C./21 mbar) a residue was obtained that after purification on silica gel column (eluant n-hexane: ethyl acetate 90/10 v/v) gives 8.0 g (0.037 moles) of 1-acetyl-6-propyl-3,4-dimethoxybenzene.

$^1$H NMR (400 MHz; $CDCl_3$): δ: 0.93 (t, 3H, J=7.5 Hz); 1.62 (m, 2H, J=7.5 Hz); 2.50 (s, 3H); 2.68 (t, 2H, J=7.5 Hz); 3.83 (s, 3H); 3.84 (s,3H); 7.07 (s, 1 H); 7.51 (s, 1 H).

$^{13}$C-NMR ($CDCl_3$, 100MHz) δ13.80, 24.54, 29.63, 37.48, 56.15, 56.42, 110.53, 111.86, 117.98, 128.85, 147.59, 154.03, 201.72.

b) Synthesis of 1-hydroxy-6-propyl-3,4-dimethoxybenzene

The product was then added with 18 ml of dichloromethane and with 7.2 g (0.15 moles) of formic acid (95% w/w): the mixture was heated to reflux and 22.3 g (0.208 moles) of hydrogen peroxide (35% w/w) were added dropwise.

After cooling and washing, the organic phase was separated and evaporated u.v. (20° C./21 mbar).

The residue was dissolved in an aqueous solution of (20% w/w) of sodium hydroxide (g.6.5).

After stirring 1 hr at room temperature the aqueous phase was washed with dichloromethane. After separation of the organic phase, the aqueous phase was acidified with a aqueous HCl till acidic pH (1-1.5). After extraction of the aqueous solution with dichloromethane, the organic phase was dried on sodium sulphate and evaporated u.v. (20° C./21 mbar). The residue was distilled at 104-112° C./0-1 mbar to give 6.1 g of a product that after crystallisation with isopropyl ether (7 ml)

gave 5.2 g of white solid product with m.p. 71-73° C., whose NMR and MS analyses corresponded to those of the aforementioned compound $^1$H NMR (400 MHz; CDCl$_3$): δ: 0.97 (t, 3H, J=7.2 Hz); 1.61 (m, 2H, J=7.2 Hz); 2.50 (t, 2H, J=7.3 Hz); 3.805 (s, 3H); 3.82 (s, 3H); 6.42 (s, 1H); 6.63 (s, 1H).

$^{13}$C-NMR (CDCl3, 100MHz) δ13.905, 23.92, 31.60, 55.94, 56.63, 100.84, 113.86, 118.95, 142.93, 147.17, 147.83.

Following the procedure as in Example 3B, the same product can be obtained starting from 1-hydroxy-3,4-dimethoxybenzene and allyl bromide, Claisen rearrangement and hydrogenation b) Synthesis of
1-(propargyloxy)-6-propyl-3,4-dimethoxybenzene Following the same procedure as in Example 3 b), 3.92 g (0.02 moles) of 1-hydroxy-6-propyl-3,4-dimethoxybenzene were reacted with 3.0 g (0.02 moles) of a solution of propargyl bromide in toluene (80% w/w) and 2.8 g (0.02 moles) of anhydrous potassium carbonate in 20 ml of acetone.

After the work up of the reaction as in Example 3 b), the residue was purified on silica gel column (eluent n-hexane:ethyl acetate 5:1 v/v) giving 3.85 g of a white solid product with m.p. 46-48° C. and whose NMR and MS analyses corresponded to those of the aforementioned compound.

$^1$H NMR (400 MHz; CDCl$_3$): δ: 0.926 (t, 3H, J=7.6 Hz); 1.5715 (sest., 2H, J=7.6 Hz); 2.484 (t, 1H, J=2.4 Hz); 2.525 (t, 2H, J=7.6 Hz); 3.811 (s, 3H); 3.836 (s, 3H); 4.623 (d, 2H, J=2.4 Hz); 6.648 (s, 1H); 6.667 (s, 1H).

$^{13}$C NMR (100MHz; CDCl$_3$): δ: 13.845 (CH$_3$); 23.449 (CH$_2$); 31.548 (CH$_2$); 55.994 e 56.287 (2 CH$_3$); 57.409 (CH$_2$); 75.040 (CH); 79.155 (Cq); 100.094 (CH); 113.685 (CH); 123.744 (Cq); 143.641 (Cq); 147.195 (Cq); 149.308 (Cq).

Example 8

Synthesis of
1-(but-2-ynyloxy)-6-propyl-3,4-dimethoxybenzene

Following the same procedure as in Example 7a) and 7b), 3.92 g (0.02 moles) of 1-hydroxy-6-propyl-3,4-dimethoxybenzene were reacted with 2.66 g (0.02 moles) of 1-bromo-2-butyne and 2.8 g (0.02 moles) of anhydrous potassium carbonate in 20 ml of acetone.

After the work up of the reaction as in Example 3 b), the residue was purified on silica gel column (eluant n-hexane:ethyl acetate 6:1 v/v) giving 3.85 g of a thick oil (125-130° C./3 mbar) whose NMR and MS analyses corresponded to those of the aforementioned compound.

$^1$H NMR (400 MHz; CDCl$_3$): δ: 0.913 (t, 3H, J=7.6 Hz); 1.5585 (sest., 2H, J=7.6 Hz); 1.807 (t, 3H, J=2.4 Hz); 2.505 (t, 2H, J=7.6 Hz); 3.791 (s, 3H); 3.820 (s, 3H); 4.560 (q, 2H, J=2.4 Hz); 6.638 (s, 1H); 6.649 (s, 1H).

$^{13}$C NMR (100 MHz; CDCl$_3$): δ: 3.348 (CH$_3$); 13.777 (CH$_3$); 23.351 (CH$_2$); 31.467 (CH$_2$); 55.900 e 56.228 (2 CH$_3$); 57.924 (CH$_2$); 74.598 (Cq); 82.999 (Cq); 100.077 (CH); 113.613 (CH); 123.544 (Cq); 143.322 (Cq); 147.110 (Cq); 149.542 (Cq).

Example 9

Synthesis of of 5-[2-(2-butoxyethoxy)-ethoxy]methyl-6-(but-2-ynyloxy)-benzo[1.3]dioxole a) Synthesis of 5-[2-(2-butoxyethoxy)-ethoxy] benzo[1.3]dioxole 34.04 g (0.105 moles) of 2-(2-butoxyethoxy)-ethyl tosylate (95%) were reacted with 14.5 g (0.105 moles) of 5-hydroxy-benzo[1.3]dioxole and 14.5 g (0.105 moles) of anhydrous potassium carbonate in 125 ml of acetone. The mixture was heated to reflux for 2 hrs, cooled to room temperature and kept, under stirring, at that temperature for 6 hrs. The mixture was then filtered and the organic solution was evaporated u.v. (20° C./21 mbar). The residue was diluted with 100 ml of dichloromethane and washed with 12 ml of an aqueous solution of sodium hydroxide 1N and water. The organic phase was separated, washed with water and evaporated u.v (20° C./21 mbar). An oil residue was obtained that was purified on silica gel column (eluant n-hexane:ethyl acetate 4:1 v/v). After evaporation 14.84 g (97.43%) of 5-[2-(2-Butoxy-ethoxy)-ethoxy]-benzo[1,3]dioxole were obtained whose NMR and MS analyses corresponded to those of the aforementioned compound.

GC-MS: m/z 282 (M$^+$, 56%).138 (100%).

$^1$H NMR (400 MHz; CDCl$_3$): δ: 0.91 (t, 3H, J=7.3 Hz); 1.36 (m, 2H, J=7.3 Hz); 1.57 (m, 2H, J=7.3 Hz); 3.47 (t, 2H, J=7.3 Hz); 3.60 (m, 2H); 3.69 (m, 2H); 3.81 (t, 2H, J=5 Hz); 4.04 (t, 2H, J=5 Hz); 5.89 (s, 2H); 6.33 (dd, 1H, J=8.6 e 2.4 Hz); 6.51 (d, 1H, J=2.4 Hz); 6.68 (d, 1H, J=8.6 Hz).

$^{13}$C-NMR (CDCl$_3$, 100MHz): δ: 13.80, 19.15, 31.59, 68.31, 69.64, 69.98, 70.71, 71.12, 98.19, 100.97, 105.71, 107.72, 141.60, 148.06, 154.18.

b) Synthesis of 1-{6-[2-(2-Butoxy-ethoxy)-ethoxy]-benzo[1,31]dioxol-5-yl}-ethanone A mixture of 14.84 g (0.05 moles) of 5-[2-(2-butoxy-ethoxy)-ethoxy]-benzo[1,3]dioxole, acetic anhydride (5.22 g, 0.056 moles) and ZnCl2 (0.7 g, 0.0052 moles) were heated to reflux for 6 hrs, cooled to room temperature and kept at room temperature for further 4 hrs.

The mixture was washed with water and dichloromethane (25 ml) was added. The organic solution was evaporated u.v. (20° C./21 mbar) and the residue was purified on silica gel column (eluant n-hexane:ethyl acetate 4:1 v/v) giving 9.02 g of a liquid product (98%) whose NMR and MS analyses corresponded to those of the aforementioned compound.

GC-MS: m/z 324 (M$^+$, 75%), 57 (62%), 165 (100%), 180 (82%).

$^1$H NMR (400 MHz; CDCl$_3$): δ: 0.91 (t, 3H, J=7.3 Hz); 1.36 (m, 2H, J=7.3 Hz); 1.56 (m, 2H, J=7.3 Hz); 2.61 (s, 3H); 3.45 (t, 2H, J=7.3 Hz); 3.59 (m, 2H); 3.68 (m, 2H); 3.88 (t, 2H, J=4.8 Hz); 4.17 (t, 2H, J=4.8 Hz); 5.97 (s, 2H); 6.52 (s, 1H); 7.32 (s, 1 H).

$^{13}$C-NMR (CDCl$_3$, 100MHz): δ: 13.77, 19.14, 31.56, 32.00, 68.70, 69.38, 70.01, 70.67, 71.12, 95.09, 101.82, 108.80, 120.83, 141.69, 152.25, 156.22, 197.11.

c) Synthesis of
5-[2-(2-butoxyethoxy)-ethoxy]methyl-6-hydroxy-benzo[1.3]dioxole 9.0 g (27 mmoles) of 1-{6-[2-(2-Butoxy-ethoxy)-ethoxy]-benzo[1,3]dioxol-5-yl}-ethanone were diluted in 20 ml of dichloromethane and added with 7.5 g (155 mmoles) of formic acid (95%).

The mixture was heated to reflux and 11.4 g (117 mmoles) of hydrogen peroxide (35%) were added dropwise. The organic phase was separated and the solvent evaporated u.v. (20° C./21 mbar). The residue was purified on silica gel column (eluant n-hexane:ethyl acetate 4:1 v/v). The product so obtained was dissolved in an aqueous solution of (20% w/w) of sodium hydroxide (5.4 g).

The aqueous mixture was then stirred at room temperature for 1 hr and was washed with 5 ml of dichloromethane. After separation of the organic phase the aqueous solution was then acidified with an aqueous HCl till acidic pH (1-1.5), and extracted with dichloromethane. The organic phase was separated and evaporated u.v. (20° C./21 mbar). The residue was then purified on silica gel column (eluant n-hexane:ethyl acetate 4:1 v/v) giving 3.06 g, (97.3%) of 5-hydroxy-[2-(2-butoxyethoxy)-ethoxy]methyl-benzo[1,3]dioxole, whose NMR and MS analyses corresponded to those of the aforementioned compound.

GC-MS: m/z 298 (M+, 69%), 57 (56%), 154 (100%), 180 (31%).

$^1$H NMR (400 MHz; CDCl$_3$): δ: 0.91 (t, 3H, J=7.2 Hz); 1.37 (m, 2H, J=7.2 Hz); 1.58 (m, 2H, J=7.2 Hz); 3.48 (t, 2H, J=7.2 Hz); 3.62 (m, 2H); 3.70-3.75 (m, 4H); 4.07 (m, 2H)); 5.85 (s, 2H); 6.52 (s, 1 H); 6.57 (s, 1 H), 6.71 (br s, 1 H, OH).

$^{13}$C-NMR (CDCl$_3$, 100MHz): δ: 13.85, 19.18, 31.56, 69.38, 69.82, 70.60, 71.24, 72.38, 97.93, 100.31, 100.85, 139.10, 139.82, 143.07.

d) Synthesis of 5-[2-(2-butoxyethoxy)-ethoxy]methyl-6-(but-2-ynyloxy)-benzo[1.3]dioxole A mixture of 3.06 g (10 mmoles) of 6-[2-(2-Butoxyethoxy)-ethoxy]-5-hydroxy-benzo[1,3]dioxole, 0.30 g (0.20 mmoles) of anhydrous potassium carbonate in ml 10 of acetone was added with 3.04 g (20 mmoles) of 1-bromo-2-butyne. The mixture was heated to reflux for 3.5 hrs. The mixture was filtered and the solvent evaporated u.v. (20° C./21 mbar). The residue was purified on silica gel column (eluant n-hexane:ethyl acetate 4:1 v/v). After evaporation of the solvent u.v. (20° C./21 mbar) 1.34 g of a liquid product was obtained, whose NMR and MS analyses corresponded to those of the aforementioned compound.

m/z 351.1 [(M+H)+, 29%], 58 (56%), 121 (60%), 298 (100%).

$^1$H NMR (400 MHz; CDCl$_3$): δ: 0.91 (t, 3H, J=7.2 Hz); 1.36 (m, 2H , J=7.2 Hz); 1.58 (m , 2H , J=7.2 Hz) ; 1.84 (t, 3H , J=2.4); 3.47 (t, 3H, J=7.2 Hz); 3.59-3.61 (m, 2H); 3.70-3.72 (m , 2H); 3.82 (t, 2H, J=5 Hz); 4.1 (t, 2H, J=5 Hz); 4.61 (q, 2H, J=2.4 Hz); 5.89 (s, 2H); 6.61 (s.1H); 6.69 (s, 1H).

$^{13}$C-NMR (CDCl$_3$, 100MHz): δ: 3.64, 13.86, 19.23, 31.67, 59.26, 69.78, 70.08, 70.44, 70.76, 71.20, 99.38, 100.50, 101.12, 141.41, 142.13, 142.64, 144.20.

Example 10

Synthesis of 5-(but-2-ynyloxy)-2,3-dihydrobenzofuran a) Synthesis of 5-acetyl-2,3-dihydrobenzofuran A mixture of 44.4 g (0.37 moles) of 2,3-dihydrobenzofuran and 37.8 g (0.37 moles) of acetic anhydride were added with 5.0 g (37 mmoles) of anhydrous zinc chloride. The mixture was heated to 95-105° C. for 10 hrs; after cooling to room temperature the mixture is added with 50 ml of water and 50 ml of dichloromethane. The organic phase was separated and the aqueous phase was extracted twice with dichloromethane (2× 30 ml). The organic phases were collected together, and washed with 50 ml of a saturated aqueous solution of sodium carbonate. The organic phase was separated and evaporated u.v. (20° C./21 mbar). The residue was then distilled at 99-100° C./0.08 mbar obtaining 14.5 g (0.089 moles) of 5-acetyl-2,3-dihydrobenzofuran.

$^1$H NMR (400 MHz; CDCl$_3$): δ: 2.50 (s, 3H); 3.20 (t, 2H, J=8.7 Hz); 4.64 (t, 2H, J=8.7 Hz); 6.76 (d, 1H, J=8.4 Hz); 7.76 (m, 1H); 7.81 (m, 1H).

$^{13}$C-NMR (CDCl$_3$, 100MHz): δ: 26.22; 28.79; 72.02; 108.72; 125.34; 127.50; 130.17; 130.48; 164.19; 196.41.

b) Synthesis of 5-hydroxy-2,3-dihydrobenzofuran

The product so obtained was added to 60 ml of dichloromethane and to 16.4 g (0.36 moles) of formic acid (title 95% w/w) and the mixture was heated to reflux; 26.3 g 0.27 moles) of hydrogen peroxide (title 35% w/w) were then added drop wise and stirred for further 3 hrs.

The mixture was then cooled to room temperature and the organic phase was separated; the aqueous phase was extracted twice with dichloromethane (2× 30 ml). The organic phases were collected together, and washed with 50 ml of a saturated aqueous solution of sodium carbonate. The solution was evaporated u.v (20° C./21 mbar). The residue was dissolved in an aqueous solution of 26.2 g of sodium hydroxide 32% (% w/w). The mixture was stirred at r.t for 1 hr; 80 ml of water were then added and the organic phase was separated off. The aqueous phase was washed with 30 ml of dichloromethane and then acidified with a solution of aqueous HCl until acid pH (1-1.5). The aqueous solution was then extracted twice with 25 ml of dichloromethane, being the organic phases collected and dried on sodium sulphate. The organic solution was then evaporated u.v. (20° C./21 mbar) and the residue was crystallised from a mixture 7/3 (v/v) of n-hexane/ethyl acetate (150 ml) giving 12.8 g of a product with m.p. 112-114 ° C. and whose NMR and MS analyses corresponded to those of the aforementioned compound.

$^1$H NMR (400 MHz; CDCl$_3$): δ: 3.16 (t, 2H, J=8.7 Hz); 4.53 (t, 2H, J=8.7 Hz); 4.72 (br s, 1 H, OH); 6.56 (dd, 1 H, J=8.6 Hz, J=2.6 Hz); 6.63 (d, 1 H, J=8.6 Hz); 6.72 (d, 1H, J=2.6 Hz).

$^{13}$C-NMR (CDCl$_3$, 100 MHz): δ: 30.14; 71.23; 109.22; 112.35; 114.12; 128.10; 149.52; 153.91.

c) Synthesis of 5-(but-2-ynyloxy)-2,3-dihydrobenzofuran

Following the same procedure as in Example 2), a mixture of 4.0 g (0.029 moles) of 5-hydroxy-2,3-dihydrobenzofuran, 4.0 g (0.029 moles) of anhydrous potassium carbonate in ml 25 of acetone was added with 3.9 g (0.029 moles) of 1-bromo-2-butyne. The mixture was heated to reflux for 6 hrs. After cooling to room temperature, the mixture was filtered and the filtrate evaporated u.v (20° C./ 21 mbar). The residue so obtained was purified by chromatography on silica column (eluant n-hexane/ethyl acetate 5/1 (v/v))

A liquid product (3.8 g purity 97.5%) was obtained, whose NMR and MS analyses corresponded to those of the aforementioned compound.

GC-MS: m/z 188 (M+, 27%), 135 (100%), 52 (35%).

$^1$H NMR (400 MHz; CDCl$_3$): δ: 1.84 (t, 3H, J=2.6 Hz); 3.14 (t, 2H, J=8.7 Hz); 4.495 (t, 2H, J=8.7 Hz,); 4.545 (q, 2H, J=2.6 Hz); 6.68 (m, 2H); 6.825 (m, 1H).

$^{13}$C NMR (100 MHz; CDCl$_3$): δ: 3.37; 29.95; 57.12; 71.00; 74.30; 83.05; 108.76; 112.28; 113.89; 127.68; 151.97; 154.39.

Example 11 Synthesis of 6-(but-2-ynyloxy)-5-propyl-2,3-dihydrobenzofuran a) Synthesis of 5-propyl-6-acetyl-2,3-dihydrobenzofuran Following the same procedure as in Example 3a), 46.3 g (0.286 moles) of 5-propyl-2,3-dihydrobenzofuran were reacted with 29.2 g (0.286 moles) of acetic anhydride and 3.9 g (0.029 moles) of anhydrous zinc chloride. After washing and work up, 18.2 g of 5-propyl-6-acetyl-2,3-dihydrobenzofuran was obtained as an oil (129-131° C./0.5 mbar) (title 93%).

$^1$H NMR (400 MHz; CDCl$_3$): δ: 0.94 (t, 3H, J=7.6 Hz); 1.585 (sest, 2H, J=7.6 Hz); 2.51 (t, 2H, J=7.6 Hz); 2.54 (s, 3H); 3.22 (t, 2H, J=8.7 Hz); 4.66 (t, 2H, J=8.7 Hz); 7.18 (s, 1H); 7.49 (s, 1H).

$^{13}$C NMR (100 MHz; CDCl$_3$): δ: 13.66; 24.73; 29.05; 30.89; 37.14; 71.90; 120.15; 127.33; 129.13; 129.91; 134.69; 158.66; 197.24.

b) Synthesis of 5-propyl-6-hydroxy-2,3-dihydrobenzofuran The product so obtained was added to 40 ml of dichloromethane and to 14.4 g (0.30 moles) of formic acid (title 95% w/w) and the mixture was heated to reflux; 22.0 g (0.223 moles) of hydrogen peroxide (title 35% w/w) were then added slowly and stirred for further 3 hrs.

The mixture was then cooled to room temperature and the organic phase was separated; the aqueous phase was extracted twice with dichloromethane (2× 30 ml). The organic phases were collected together, and washed with 50 ml of a saturated aqueous solution of sodium carbonate. The solution was evaporated u.v (20° C./21 mbar) and the residue was dissolved in a methanol/water solution (1:5 v/v). The mixture was cooled at 4-5° C. and added with an aqueous solution of 9.3 g of sodium hydroxide 32% (% w/w). The mixture was stirred at room temperature for 1 hr; 80 ml of dichloromethane were then added and the organic phase was separated off.

The aqueous phase was washed with 40 ml of dichloromethane and then acidified with a solution of aqueous HCl until acid pH (1-1.5). The aqueous solution was then extracted twice with 25 ml of dichloromethane, being the organic phases collected and dried on sodium sulphate. The organic solution was then evaporated u.v. (20° C./21mbar) and the residue was crystallised from a mixture 4/1 (v/v) of n-hexane/isopropyl ether (30 ml) giving 8.5 g of a product (title 93.5% with m.p. 77-79° C. and whose NMR and MS analyses corresponded to those of the aforementioned compound.

$^1$H NMR (400 MHz; CDCl$_3$): δ: 0.93 (t, 3H, J=7.6 Hz); 1.59 (sest, 2H, J=7.6 Hz); 2.48 (t, 2H, J=7.6 Hz); 3.21 (t, 2H, J=8.7 Hz); 4.59 (t, 2H, J=8.7 Hz); 5.45 (br s, 1H, OH); 6.57 (s, 1H); 6.60 (s, 1H).

$^{13}$C NMR (100 MHz; CDCl$_3$): δ: 13.75; 24.88; 30.52; 37.57; 71.92; 114.88; 116.59; 127.59; 130.34; 139.72; 144.57.

c) Synthesis of 6-(but-2-ynyloxy)-5-propyl-2,3-dihydrobenzofuran

Following the same procedure as in Example 3 c), a mixture of 5.0 g (0.026 moles) of 5-propyl-6-hydroxy-2,3-dihydrobenzofuran (title 93.5%), 3.9 g (0.028 moles) of anhydrous potassium carbonate in ml 30 of acetone was added with 3.7 g (0.028 moles) of 1-bromo-2-butyne: the mixture was heated to reflux for 6 hrs. After cooling to room temperature, the mixture was filtered and the filtrate evaporated u.v (20° C./21 mbar). The residue so obtained was purified by chromatography on silica column (eluant n-hexane/ethyl acetate 3/1 (v/v)). A liquid product (3.8 g, purity 96%) was obtained, whose NMR and MS analyses corresponded to those of the aforementioned compound.

GC-MS: m/z 230 (M$^+$, 70%), 201 (48%), 177 (84%) 52 (100%).

$^1$H NMR (400 MHz; CDCl$_3$): δ: 0.935 (t, 3H, J=7.6 Hz); 1.585 (sest, 2H, J=7.6 Hz); 1.815 (t, 3H, J=2.6 Hz); 2.51 (t, 2H, J=7.6 Hz); 3.15 (t, 2H, J=8.7 Hz); 4.55 (t, 2H, J=8.7 Hz); 4.685 (q, 2H, J=2.6 Hz); 6.66 (s, 2H).

$^{13}$C NMR (400 MHz; CDCl$_3$): δ: 3.33 (CH$_3$); 13.43 (CH$_3$); 24.68 (CH$_2$); 30.01 (CH$_2$); 37.47 (CH$_2$); 57.46 (CH$_2$); 71.37 (CH$_2$); 74.10 (Cq); 83.28 (Cq); 113.88 (CH); 117.52 (CH); 127.99 (Cq); 135.20 (Cq); 141.68 (Cq); 146.53 (Cq).

Example 12

Activity on MFO Enzymes

In vivo studies on peach-potato aphid, *Myzus persicae* (Sulzer) (*Hemiptera: Aphididae*)

12.1 Material and Methods 12.1.1 Aphid Clone

Aphid clones were reared on Chinese cabbage (*Brassica rapa L.* var. Pekinensis c.v Wong Bok) (*Brassicaceae*) leaves held in small plastic box-cages maintained at 18±2° C. with a 16:8 h light:dark photoperiod (Blackman R L, Variation in the photoperiodic response within natural populations of Myzus persicae (Sulzer). *Bull Ent Res* 60: 533-546 (1971)).

Clone 4106A is a laboratory insecticide-susceptible standard2 . Clone 5191A is a highly resistant (R3) clone possessing the FE4 variant of enhanced esterase; it was collected in Greece in2007 from tobacco. Both aphid clones have been established from single parthenogenetic *M. persicae* females (Foster S P, Denholm I, Thompson R, Poppy G M, Powell W, Reduced response of insecticide-resistant aphids and attraction of parasitoids to alarm pheromone; a potential fitness trade-off. *Bull Ent Res* 95: 37-46 (2005)).

12.1.2 Topical Application Bioassay with 5191A Aphid Clone Young apterae were transferred to the abaxial surface of Chinese cabbage leaf discs (10 adults per leaf disc, at least 3 replicates per concentration) held on 1% agar in plastic containers (4 cm in diameter). The upper edge of each container was coated with Fluon (Whitford Plastics, UK) to prevent subsequent aphid escape from the leaf surface. After allowing 2 h for the aphids to settle, each was dosed with 0.25 μl of either 1 g L$^{-1}$ Compound of Example 3 dissolved in acetone or acetone only. After 4 h aphids were further treated with 0.25 μl imidacloprid in acetone (96% AR) using a Burkard microapplicator (Burkard, Rickmansworth, UK). Controls were treated with acetone only. Treated aphids were stored at 18±2° C. and 16 h light: 8 h dark photoperiod. All bioassays were scored at the endpoint of 72 h after treatment. Adults incapable of co-ordinated movement (after gentle touching with a paint brush if necessary) were scored as dead. All bioassays were completed in triplicate.

12.2 Results

Table 1 shows the effect of using the novel composition of a synergist (Compound of Example 3) as a pre-treatment to imidacloprid. The efficacy was increased against the resistant clone, 5191A, compared to the susceptible clone 4106A. In this example, the resistant clone exhibits a 56.5 resistance factor (RF) to imidacloprid compared with the susceptible clone.

TABLE 1

In vivo results of aphid clones using Compound of Example 3 as a pre-treatment

| Treatment | Aphid Clone | Resistant Status Esterase variant (level) | LC$_{50}$ (ppm) | 95% CL | Slope (±SE) | df | X$^2$ | RF | SF |
|---|---|---|---|---|---|---|---|---|---|
| imidacloprid | 4106A | S | 1.6 | 1.2-1.9 | 1.9 (±0.16) | 60 | 83 | 1 | — |
|  | 5191A | FE4(R3) | 90.5 | 51-185 | 0.9 (±0.07) | 58 | 193 | 56.5 | — |
| imidacloprid plus Compound of Example 3 (1 g L$^{-1}$) | 5191A | FE4(R3) | 1.25 | 0.75-1.9 | 1.2 (±0.08) | 77 | 268 | — | 72.4 |

LC$_{50}$ = Lethal concentration of imidacloprid to kill 50% of the population.
CL = Confidence limits
SE = Standard error
df = degree of freedom
X$^2$ = chi-square value
RF = Resistance factor (LC$_{50}$ for the resistant population divided by the LC$_{50}$ for the susceptible population)
SF = synergism factor (LC$_{50}$ unsynergised divided by the LC$_{50}$ synergised)

Example 13

In Vitro Studies on Peach-potato Aphid, *Myzus persicae* (Sulzer) (*Hemiptera: Aphididae*)
Esterase Inhibition
13.1 Material and Methods
13.1.1 Aphid Clone Clones 794JZ is laboratory standard resistant variants possessing R3 levels of E4. (Foster S P, Denholm I, Thompson R, Poppy G M, Powell W, Reduced response of insecticide-resistant aphids and attraction of parasitoids to alarm pheromone; a potential fitness trade-off. *Bull Ent Res* 95: 37-46 (2005)).

13.1.2 Esterase Inhibition Assay

Measuring the in vitro inhibition is not straight forward, as synergists may bind to a site other than the active site. For this reason an indirect measurement was performed using the 'esterase interference assay', as described by Khot et al., (2008) (Khot A C, Bingham G, Field L M, Moores G D, A novel assay reveals the blockade of esterases by piperonyl butoxide. *Pest Manag Sci* 64: 1139-1142 (2008)) with some modifications.

13.1.2.1 Esterase Purification

The esterase used was the well-characterised resistance associated esterase purified from *M. persicae*, E4, (aphid clone: 794JZ) as per Devonshire (1977) with some modifications(Devonshire A L, The properties of a carboxylesterase from the peach-potato aphid, *Myzus persicae* (Sulz.) and its role in conferring insecticide resistance. *Biochem J* 167: 675-683 (1977)). Briefly, 5 g of aphids (stored at −20° C.) were homogenised in 0.02 M phosphate buffer pH 7.0 and centrifuged at 20 000 g for 10 min. The supernatant was passed through a G-25 column using 0.02M Tris/HCl, pH 8.5 buffer. Unretarded fractions containing esterase activity were further chromatographed through DEAF Sepharose Fast Flow (Amersham Biosciences) and eluted with a linear 0-0.35 M NaCl gradient in 500 ml of Tris/HCl as above. Fractions containing carboxylesterase activity in the form of E4 were concentrated, desalted, and buffer exchanged to 0.02 M phosphate pH 7.0 for storage.

13.1.2.2 Indirect Determination of Esterase Inhibition

Interactions of the purified resistance-associated esterase (E4) with Compound of Example 2, Compound of Example 3, Compound of Example 4, Compound of Example 9 and Compound of Example 11 were performed using the 'esterase interference assay', as described by Khot et al., with some modifications. Devonshire A L, The properties of a carboxylesterase from the peach-potato aphid, *Myzus persicae* (Sulz.) and its role in conferring insecticide resistance. *Biochem J* 167: 675-683 (1977)). Briefly, stock solutions of novel synergists (3 mM in acetone) were pre-incubated with pure E4, to give a final concentration of 0.03 mM, for 16 h at 4° C. Aliquots (15 µl) of E4, E4+Compound of Example 2, E4+Compound of Example 3, E4+Compound of Example 4, E4+Compound of Example 9 and E4+Compound of Example 11 were incubated for 1 h with 60 µl of serial dilutions of azamethiphos in 0.02M phosphate buffer, pH 7, in separate wells of a NUNC microplate. Aliquots (25 pl) of house fly head homogenate (source of AChE) were added to each well and incubated for 15 minutes at room temperature. E4 in acetone and buffer only served as the positive and the negative controls respectively. AChE activity was measured at 405 nm using a Tmax kinetic microplate reader (Molecular Devices, Menlo Park, Calif.). Readings were taken automatically for 10 min at 10 s intervals. The rate (mOD min$^{-1}$) was calculated by the integrated software, Softmax Pro 4.6. All treatments were performed in triplicate.

13.2 Results

Figure 1:
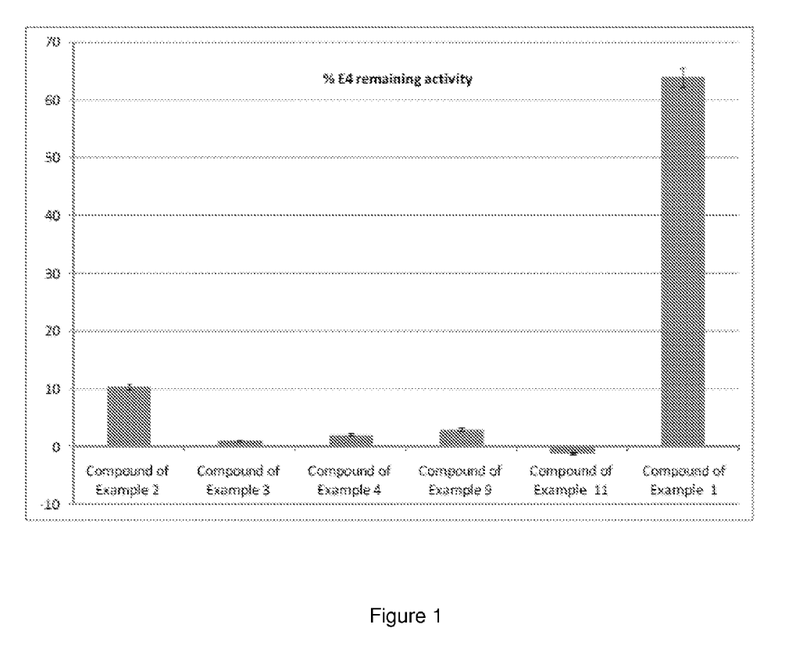
In FIG. 1 the results of the reduced esterase protection (%) after pre-incubation with all compounds of the Example 13 (Compounds of Examples 2, 3, 4, 9, 11 of the invention and the compound of the comparative Example 1) are represented.

The reduced esterase protection (%) after pre-incubation with all Compounds (Compound of Example 2,3,4,9 and 11) are presented in Table 2. and FIG. 1.

No added esterase is giving 0% esterase protection and uninhibited esterase (E4) is giving 100% protection.

TABLE 2

Reduced esterase protection (%) after pre-incubation with all Compounds

| Compound | Esterase protection (%) | ±SE |
|---|---|---|
| No esterase | 0 |  |
| E4 | 100 |  |
| Compound of Example 2 | 10.36 | 0.5 |
| Compound of Example 3 | 0.97 | 0.13 |
| Compound of Example 4 | 2.06 | 0.18 |
| Compound of Example 9 | 2.96 | 0.25 |
| Compound of Example 11 | −1.17 | 0.12 |
| Compound of Example 1 | 63.9 | 1.73 |

The values of the reduced esterase protection (%) after pre-incubation with all Compounds have been represented in FIG. 1. The compounds of the composition of the invention reduced the esterase protection much more strongly than a composition comprising the compound of the prior art (compound of Example 1). Furthermore, the compound of example 4, having an hydrogen instead of a methyl in R5 showed worse activity than the compound of Example 3.

Example 14

In vivo studies on pollen beetle, Meligethes aeneus (Fabricious) (Coleoptera: Nitidulidae)

14.1. Material and Methods 14.1.1 Pollen Beetle Populations

Two pyrethroid resistant populations originating from two different areas in Poland 'Rogalin' and lebork' were collected in July 2008. A putative susceptible population, UK population, was also collected in July 2008 in Hertfordshire, UK. All populations were collected from oilseed rape contained adults only and were kept at room temperature before assays were performed.

14.1.2 Full Dose Response Bioassays (α-cypermethrin)

To characterise the response of the 3 above pollen beetle populations against α-cypermethrin full dose response bioassays were carried out. The bioassay method used was based on the method recommended by the Insecticide Resistance Action Committee (IRAC method no 11). Briefly, glass vials (5.7 cm height and 2.3 cm diameter) were coated with 0.5 ml of a serial dilutions of insecticide, dissolved in acetone, (α-cypermethrin) and rolled upon a blood-roller (Luckham Multimix Major, Denley Instruments Ltd) at room temperature until the solutions had completely evaporated. Five to 20 non-sexed adult pollen beetles were placed into a vial for each replicate and the top loosely closed with a screw-cap. Three replicates were used at each insecticide concentration, 7 concentrations in all. Vials treated with acetone only were used as controls.

Treated vials including the pollen beetles were stored in constant environment facilities at 18±2° C. and 16L: 8D. All bioassays were scored at an endpoint of 24 h after exposure to the insecticide. Insects incapable of coordinated movement (after gentle touching with a pencil brush if necessary) were scored as dead.

14.1.3 Discriminating Dose Bioassays

Bioassays incorporating the compounds (Compound of Example 2 and Compound of Example 3) dissolved in acetone, were carried out using a diagnostic concentration of α-cypermethrin derived from the above full dose response bioassays in a mixture of 0.01 g $L^{-1}$ of the compounds. The concentration of α-cypermethrin used for the discriminating dose bioassays was 0.3 ppm α-cypermethrin for the two polish populations, Rogalin and Lebork and 0.03 ppm α-cypermethrin for UK population. Vials treated with the compounds only, dissolved in acetone and acetone only were used as controls. Ten to 15 replicates were used for each treatment depending on insect numbers within the population. Compounds concentrations chosen conferred no mortality in preliminary bioassays.

Treated vials including the pollen beetles were stored in constant environment facilities at 18±2° C. and 16L: 8D. All bioassays were scored at an endpoint of 24 h after exposure to the insecticide. Insects incapable of coordinated movement (after gentle touching with a pencil brush if necessary) were scored as dead.

14.2. Results 14.2.1 Full Dose Response Bioassays (α-cypermethrin)

Results from full dose response bioassays with α-cypermethrin for the 3 populations, are presented in Table 3. The $LC_{50}$ value obtained from the UK population against α-cypermethrin was considered as representative of a standard susceptible population. Populations from Poland, Lebork and Rogalin, gave a relative high resistance factors (RF) of 44 and 23 respectively.

TABLE 3

In vivo results of pollen beetles assay against α-cypermethrin

| Population | $LC_{50}$ (ng/cm²) | 95% CL | Slope (±SE) | df | $X^2$ | RF |
|---|---|---|---|---|---|---|
| UK population | 2.80 | 0.19-4.50 | 1.58 (±0.185) | 26 | 42.35 | 1 |
| Rogalin | 65.0 | 40.0-100 | 1.4 (±0.2) | 18 | 11.9 | 23.21 |
| Lebork | 95.0 | 66.0-140 | 2.5 (±0.48) | 18 | 6.23 | 44 |

$LC_{50}$ = Lethal concentration of α-cypermethrin to kill 50% of the population.

CL = Confidence limits

SE = Standard error df = degree of freedom $X^2$ = chi-square value

RF = Resistance factor = $LC_{50}$ for the resistant population divided by the $LC_{50}$ for the susceptible population 14.2.1.2 Discriminating Dose Bioassays Discriminating doses of α-cypermethrin were chosen for each population, based on the results of the full-dose bioassays.

Figure 2:
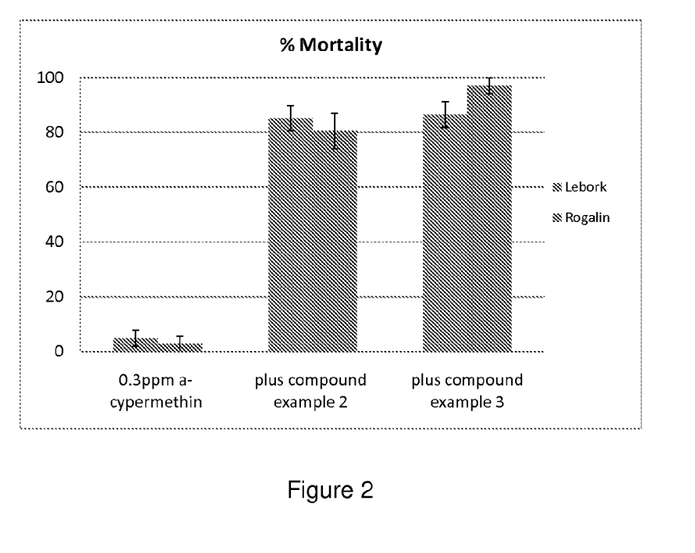
In FIG. 2 In vivo results of pollen beetles (Lebork and Rogalin from Poland) of Example 14, using a discriminating dose of a-cypermethrin and 0.01 g L$^{-1}$ Compound of Example 2 and Example 3, are represented.
Figure 3:
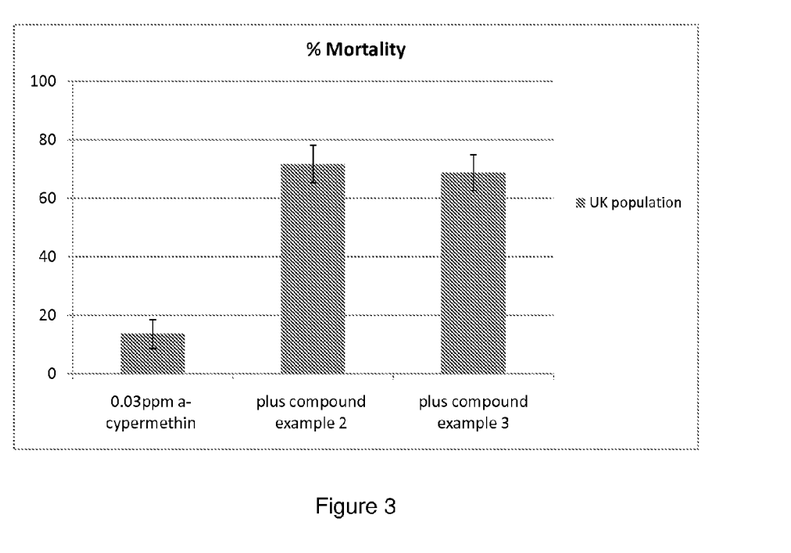
In FIG. 3 In vivo results of UK population of Example 14, using a discriminating dose of α-cypermethrin and 0.01 g L$^{-1}$ Compound of Example 2 and Example 3, are represented.

Table 4 and FIG. 2 show pollen beetle mortality after being treated with either 0.01 g $L^{-1}$ Compound of Example 2 or 0.01 g $L^{-1}$ Compound of Example 3 in a mixture with a diagnostic concentration of α-cypermethrin (0.3 ppm) against Rogalin and Lebork. Excellent synergism of α-cypermethrin with both populations was obtained by increasing the mortality from approx. 5 to around 85%. Additionally, synergism effect with α-cypermethrin was obtained by using a 10-fold less α-cypermethrin (0.03 ppm) against the susceptible population (UK population). Results for the UK population are presented in Table 5 and FIG. 3. No mortality was observed in treatments with acetone only and the compounds (Examples 2 and 3) only (data are not shown).

TABLE 4

In vivo results of pollen beetles (Lebork and Rogalin) using a discriminating dose of α-cypermethrin and 0.01 g $L^{-1}$ Compound of Example 2 and Example 3

| | Lebork | | Rogalin | |
|---|---|---|---|---|
| Treatments | % Mortality | ±SE | % Mortality | ±SE |
| 0.3 ppm ppm α-cypermethrin | 4.9 | 3.0 | 2.78 | 2.8 |
| Plus 0.01 g $L^{-1}$ Compound of Example 2 | 85.21 | 4.6 | 80.56 | 6.5 |
| Plus 0.01 g $L^{-1}$ Compound of Example 3 | 86.53 | 4.7 | 97.06 | 2.85 |

In FIG. 2. In vivo results of pollen beetles (Lebork and Rogalin) have been represented, by using a discriminating dose of α-cypermethrin and 0.01 g $L^{-1}$ Compound of Example 2 and Example 3

TABLE 5

In vivo results of UK population using a discriminating dose of α-cypermethrin and 0.01 g L$^{-1}$ Compound of Example 2 and Example 3

| Treatments | UK population | |
|---|---|---|
| | % Mortality | ±SE |
| 0.03 ppm α-cypermethrin | 13.64 | 4.95 |
| Plus 0.01 g L$^{-1}$ Compound of Example 2 | 71.68 | 6.41 |
| Plus 0.01 g L$^{-1}$ Compound of Example 3 | 68.78 | 6.13 |

Example 15

In Vitro Studies on Pollen Beetle, *Meligethes aeneus* (Fabricious) (*Coleoptera: Nitidulidae*)

The ability of the novel compositions comprising the synergists of Formula (I) to inhibit P450 enzymes, a major mechanism conferring resistance to xenobiotics, was measured using pollen beetle homogenate.

15.1 Material and Methods
15.1.1 Pollen Beetle Populations
Pollen beetle populations the same as Section C.1.1
15.1.2 Enzyme assay (Oxidase assay)
15.1.2.1 Insect Homogenisation Approximately 50 non-sexed adult pollen beetle from each population were homogenised on ice in 1 ml 0.1 M sodium phosphate buffer, pH 7.6, containing, 1 mM EDTA, 1 mM DTT, 1 mM PTU, 1 mM PMSF and centrifuged at 10 000×g for 10 min. The resulting supernatant was used as the enzyme source.

15.1.2.2 Determination of O-deethylation Inhibition

The O-deethylation inhibition by compounds of Example 2 or 3 was measured using 7-ethoxycoumarin (7-EC) according to Ullrich and Weber (Ullrich V and Weber P, The O-dealkylation of 7-ethoxycoumarin by liver microsomes. *Z Physiol Chem* 353: 1171-1177 (1972)) and adapted to the microplate format as described by DeSousa (De Sousa G, Cuany A, Brun A, Amichot M, Rahmani R, Berge J B, A microfluorometric method for measuring ethoxycoumarin-O-deethylase activity on individual *Drosophila melanogaster* abdomens: interest for screening resistance in insect populations *Analyt. Biochem* 229: 86-91 (1995)). Briefly, 7-EC was dissolved in ethanol to make a 20 mM stock solution and diluted by the addition of 0.1 M, pH 7.8 sodium phosphate buffer to give a concentration of 0.5 mM. Fifty microliters of pollen beetle enzyme were added to separate wells of a microplate, followed by the addition of 3 µl 10 mM of either compounds of Example 2 or 3 or acetone only. After 10 min incubation in room temperature, 80 µl 0.5 mM 7-EC was added following by another 5 min at 30° C. The reaction initiated by the addition of 10 µl 9.6 mM NADPH in 0.1 M sodium phosphate, pH 7.8. Enzyme activity was measured in a Victor$^2$ 1420 multilabel counter (Wallac, Milton Keynes, UK) for 60 min with readings taken every 5 min, using an excitation wavelength of 370 nm and an emission wavelength of 460 nm. All assays were performed in triplicate.

15.2 Results

The ability of the composition comprising the compounds of Examples 2 and 3 to inhibit oxidases derived from the 3 different pollen beetle populations is presented in Table 7. If enzyme activity is completely inhibited this assay often gives a negative slope due to substrate interactions.

TABLE 7

The O-deethylation inhibition by Compounds of Examples 2 and 3

| | Rogalin | | | Lebork | | | UK population | | |
|---|---|---|---|---|---|---|---|---|---|
| | Remaining activity (%) | Lower 95% CI | Upper 95% CI | Remaining activity (%) | Lower 95% CI | Upper 95% CI | Remaining activity (%) | Lower 95% CI | Upper 95% CI |
| Enzyme plus acetone | 100 | | | 100 | | | 100 | | |
| Enzyme plus 10 mM compound of Example 2 | −11.25 | −22.5 | −0.004 | −38.98 | −45.38 | −32.58 | −9.3 | −15.44 | −3.16 |
| Enzyme plus 10 mM compound of Example 3 | 27.6 | 11.42 | 43.76 | −2.24 | −12.5 | 8.02 | 10.4 | 2.93 | 17.88 |

Example 16

The materials and procedure as stated in Example 13, paragraphs 13.1, 13.1.2, 13.1.2.1 and 13.1.2.2. have been used and the following results have been obtained:

TABLE 3

Reduced esterase protection (%) after pre-incubation with all Compounds

| Compound | Esterase protection (%) | ±SE |
|---|---|---|
| No esterase | 0 | |
| E4 | 100 | |
| Compound of Example 2 | 10.35 | 0.5 |
| Compound of Example 1 | 63.90 | 1.72 |
| Compound of Example 3 | 0.98 | 0.16 |
| Compound of Example 4 | 2.06 | 0.18 |
| Compound of Example 8 | 5.09 | 0.48 |
| Compound of Example 7 | 15.17 | 1.03 |

From Table 3, it is evident that compounds of invention show better activity than compound 1. Furthermore, the compounds of invention having methyl instead of hydrogen in R5, i.e. compounds of examples 3, 8 show better activity than compounds 4, 7, respectively.

The invention claimed is:

1. A pesticidal composition comprising an alkynyl phenoxy compound of formula (I):

wherein
$R_1$ and $R_2$, similar or different, are ($C_1$-$C_4$)alkyl or $R_1O$— and $R_2O$— together represent a group —O—$CH_2$—O—, —O—$CH(CH_3)$—O—, —O—$CH_2$—$CH_2$—O—, —O—$CH_2$—$CH_2$—,
$R_3$ is ($C_1$-$C_6$)alkyl, ($C_3$-$C_6$)alkenyl or —B—($CH_2$—$CH_2$—O)z-$R_6$ where B is —$CH_2$—O— or —O—, z is 0, 1 or 2 and $R_6$ is ($C_1$-$C_4$)alkyl;
$R_4$ is hydrogen or methyl;
$R_5$ is hydrogen or methyl;
x is an integer from 1 to 2;
y is 0, 1 or 2;
with the proviso that
5-(propargyloxy)-benzo[1,3]dioxole is excluded, and when $R_3$ is —B—($CH_2$—$CH_2$—O)z-$R_6$, y is 1
as a synergist and a pesticidal active ingredient.

2. The composition according to claim 1, wherein in the alkynyl phenoxy compound of Formula (I) x is 1.

3. The composition according to claim 1, wherein in the alkynyl phenoxy compound of Formula (I) y is 1.

4. The composition according to claim 1, wherein in the alkynyl phenoxy compound of Formula (I) $R_1$ and $R_2$, independently each other, denote methyl, ethyl or $R_1O$— and $R_2$— together represent a group —O—$CH_2$—O— or —O—$CH_2$—$CH_2$—.

5. The composition according to claim 4, wherein in the alkynyl phenoxy compound of Formula (I) $R_1$ and $R_2$ are methyl or $R_1O$— and $R_2$— together represent a group —O—$CH_2$—O—.

6. The composition according to claim 5, wherein in the alkynyl phenoxy compound of Formula (I) $R_3$ is ($C_3$-$C_6$)alkyl or ($C_3$-$C_6$)alkenyl and when y is 1, $R_3$ is a group —$CH_2$—O—($CH_2$—$CH_2$—O)$_2$—$C_4H_9$ or a group —O—($CH_2$—$CH_2$—O)$_2$—$C_4H_9$.

7. The composition according to claim 1, wherein in the alkynyl phenoxy compound of Formula (I) $R_3$ is propyl, 1-propen-3-yl or 2-propen-3-yl, or, when y is 1, a group —O—($CH_2$—$CH_2$—O)$_2$—$C_4H_9$.

8. The composition according to claim 1, wherein in the alkynyl phenoxy compound of Formula (I) $R_5$ is methyl.

9. The composition according to claim 1 wherein the compound of Formula (I) is selected from the group consisting of:
5-(but-2-ynyloxy)-benzo[1.3]dioxole
5-(but-2-ynyloxy)-6-propyl-benzo[1.3]dioxole
5-(propargyloxy)-6-propyl-benzo[1.3]dioxole
1-(propargyloxy)-6-propyl-3,4-dimethoxybenzene
1-(but-2-ynyloxy)-3,4-dimethoxybenzene
1-(propargyloxy)-6-propyl-3,4-dimethoxybenzene
1-(but-2-ynyloxy)-6-propyl-3,4-dimethoxybenzene
5-[2-(2-butoxyethoxy)-ethoxy]methyl-6-(but-2-ynyloxy)-benzo[1.3]dioxole
5-(but-2-ynyloxy)-2,3-dihydrobenzofuran
6-(but-2-ynyloxy)-5-propyl-2,3-dihydrobenzofuran.

10. The composition according to claim 9 wherein the compound of Formula (I) is selected from the group consisting of:
5-(but-2-ynyloxy)-benzo[1.3]dioxole
5-(but-2-ynyloxy)-6-propyl-benzo[1.3]dioxole
1-(propargyloxy)-6-propyl-3,4-dimethoxybenzene
1-(but-2-ynyloxy)-6-propyl-3,4-dimethoxybenzene
5-[2-(2-butoxyethoxy)-ethoxy]methyl-6-(but-2-ynyloxy)-benzo[1.3]dioxole
5-(but-2-ynyloxy)-2,3-dihydrobenzofuran
6-(but-2-ynyloxy)-5-propyl-2,3-dihydrobenzofuran.

11. The composition according to claim 10, wherein the compound of Formula (I) is selected from the group consisting of
5-(but-2-ynyloxy)-benzo[1.3]dioxole
5-(but-2-ynyloxy)-6-propyl-benzo[1.3]dioxole
5-[2-(2-butoxyethoxy)-ethoxy]methyl-6-(but-2-ynyloxy)-benzo[1.3]dioxole
6-(but-2-ynyloxy)-5-propyl-2,3-dihydrobenzofuran.

12. A pesticide formulation comprising the pesticide composition according to claim 1 and an inert carrier.

13. A method for controlling pests which provides for applying an efficacy amount of the pesticide composition according to claim 1 to pests on non-animal biotopes.

14. A method for the treatment of pests on animal biotopes comprising the step of applying the pesticide composition of claim 1.

15. 5-(but-2-ynyloxy)-benzo[1.3]dioxole (ex.2).

16. 5-(but-2-ynyloxy)-6-propyl-benzo [1.3] dioxole (ex.3).

17. 1-(propargyloxy)-6-propyl-3,4-dimethoxybenzene (ex .7).

18. 1-(but-2-ynyloxy)-6-propyl-3,4-dimethoxybenzene (ex.8).

19. 5[2-(2-butoxyethoxy)-ethoxy]methyl-6-(but-2-ynyloxy)-benzo[1.3]dioxole (ex.9).

20. 5-(but-2-ynyloxy)-2,3-dihydrobenzofuran (ex.10).

21. 6-(but-2-ynyloxy)-5-propyl-2,3-dihydrobenzofuran (ex.11).

22. An alkynyl phenoxy compound of formula (I):

wherein
$R_1$ and $R_2$, similar or different, are ($C_1$-$C_4$)alkyl or $R_1O$— and $R_2O$— together represent a group —O—$CH_2$—O—, —O—$CH(CH_3)$—O—, —O—$CH_2$—$CH_2$—O—, —O—$CH_2$—$CH_2$—,
$R_3$ is ($C_1$-$C_6$)alkyl, ($C_3$-$C_6$)alkenyl or —B—($CH_2$—$CH_2$—O)z-$R_6$ where B is —$CH_2$—O— or —O—, z is 0, 1 or 2 and $R_6$ is ($C_1$-$C_4$)alkyl;
$R_4$ is hydrogen or methyl;
$R_5$ is hydrogen or methyl;
x is an integer from 1 to 2;
y is 0,1 or 2;
with the proviso that
5-(propargyloxy)-benzo[1,3]dioxole is excluded, and when $R_3$ is —B—($CH_2$—$CH_2$—O)z-$R_6$, y is 1
as a synergist for a pesticidal active ingredient.

* * * * *